United States Patent
Jaillon et al.

(10) Patent No.: US 9,200,888 B2
(45) Date of Patent: Dec. 1, 2015

(54) MULTI-CHANNEL OPTICAL COHERENCE TOMOGRAPHY

(71) Applicant: TOMEY CORPORATION, Nagoya-shi (JP)

(72) Inventors: Franck E. M. Jaillon, Nagoya (JP); Naoko Hara, Nagoya (JP); Tsutomu Ohmori, Nagoya (JP); Chihiro Kato, Nagoya (JP)

(73) Assignee: Tomey Corporation (JP)

( * ) Notice: Subject to any disclaimer, the term of this patent is extended or adjusted under 35 U.S.C. 154(b) by 52 days.

(21) Appl. No.: 14/069,626

(22) Filed: Nov. 1, 2013

(65) Prior Publication Data

US 2015/0124261 A1   May 7, 2015

(51) Int. Cl.
*G01B 9/02* (2006.01)
*A61B 3/10* (2006.01)

(52) U.S. Cl.
CPC ............ *G01B 9/02091* (2013.01); *A61B 3/102* (2013.01); *G01B 9/02019* (2013.01); *G01B 9/02027* (2013.01); *G01B 9/02028* (2013.01); *G01B 9/02045* (2013.01)

(58) Field of Classification Search
CPC ........... G01B 9/02019; G01B 9/02027; G01B 9/02045; G01B 9/02091; G01B 9/02028; G01B 9/0205; A61B 3/102; G01N 21/4795
See application file for complete search history.

(56) References Cited

U.S. PATENT DOCUMENTS

| 5,900,928 | A | 5/1999 | Riva et al. |
|---|---|---|---|
| 6,445,939 | B1 | 9/2002 | Swanson et al. |
| 6,549,801 | B1 | 4/2003 | Chen et al. |
| 6,741,359 | B2 | 5/2004 | Wei et al. |
| 2003/0020920 | A1 | 1/2003 | Dave et al. |
| 2009/0264707 | A1* | 10/2009 | Hendriks et al. .............. 600/181 |
| 2011/0242487 | A1* | 10/2011 | Yuasa et al. ................... 351/206 |

(Continued)

FOREIGN PATENT DOCUMENTS

| WO | 02/04929 | 1/2002 |
|---|---|---|
| WO | 2006/054116 | 5/2006 |

OTHER PUBLICATIONS

An et al., Optical microangiography provides correlation between microstructure and microvasculature of optic nerve head in human subjects, Journal of Biomedical Optics, vol. 17, No. 11 (Nov. 2012), pp. 116018-1, 116018-6.

(Continued)

*Primary Examiner* — Michael A Lyons
(74) *Attorney, Agent, or Firm* — Grossman Tucker Perreault & Pfleger PLLC

(57) ABSTRACT

An optical coherence tomography apparatus includes a multi-beam configuration unit comprising at least a first optical path having a first numerical aperture and a second optical path having a second numerical aperture. The multi-beam configuration unit orients the second optical path in a selected orientation in space relative to the first optical path. A scan system illuminates a sample with non-polarized light received from the multi-beam configuration unit and directs light returning from the sample to the first optical path and the second optical path. The multi-beam configuration unit directs light returning from the sample, along the first optical path and the second optical path, to an optical pathway leading to a processing system. The processing system performs optical coherence tomography motion analysis based on interference between light returning from the sample and a first reference signal.

12 Claims, 17 Drawing Sheets

(56) References Cited

U.S. PATENT DOCUMENTS

| 2012/0120408 | A1 | 5/2012 | Yasuno et al. | |
|---|---|---|---|---|
| 2012/0176613 | A1* | 7/2012 | Marple et al. | 356/301 |
| 2013/0321822 | A1* | 12/2013 | Vogler et al. | 356/497 |
| 2014/0016136 | A1* | 1/2014 | Kawano et al. | 356/479 |
| 2015/0176969 | A1* | 6/2015 | Jensen | G01B 9/02091 |

OTHER PUBLICATIONS

Blatter et al., Dove prism based rotating dual beam bidirectional Doppler OCT, Biomedical Optics Express, vol. 4, No. 7 (Jul. 1, 2013), pp. 1188-1203.
Braff et al., Angiography of the retina and the choroid with phase-resolved OCT using interval-optimized backstitched B-scans, Optics Express, vol. 20, No. 18 (Aug. 27, 2012), pp. 20516-20534.
Chinn et al., Optical coherence tomography using a frequency-tunable optical source, Optics Letters, vol. 22, Issue 5 (Mar. 1, 1997), pp. 340-342.
Choi et al., Phase-sensitive swept-source optical coherence tomography imaging of the human retina with a vertical cavity surface-emitting laser light source, Optics Letters, vol. 38, Issue 3 (Feb. 1, 2013), pp. 338-340.
Fercher et al., Measurement of intraocular distances by backscattering spectral interferometry, Optics Communications, vol. 117, Issues 1-2 (May 15, 1995), pp. 43-48.
Hendargo et al., Doppler velocity detection limitations in spectrometer-based versus swept-source optical coherence tomography, Biomed. Opt. Express, vol. 2, No. 8 (Aug. 1, 2011), pp. 2175-2188.
Jaillon et al., Variable velocity range imaging of the choroid with dual-beam optical coherence angiography, Optics Express, vol. 20, No. 1(Jan. 2, 2012), pp. 385-396.
Klein et al., Megahertz OCT for ultrawide-field retinal imaging with a 1050nm Fourier domain mode-locked laser, Optics Express, vol. 19, No. 4 (Feb. 14, 2011), pp. 3044-3062.
Makita et al., Dual-beam-scan Doppler optical coherence angiography for birefringence-artifact-free vasculature imaging, Optics Express, vol. 20, No. 3 (Jan. 30, 2012), p. 2681-2692.
Park et al., Double common-path interferometer for flexible optical probe of optical coherence tomography, Optics Express, vol. 20, No. 2 (Jan. 16, 2012), pp. 1102-1112.
Park et al., Real-time fiber-based multi-functional spectral-domain optical coherence tomography at 1.3μm, Optics Express, vol. 13, No. 11 (May 30, 2005), pp. 3931-3944.
Potsaid et al., Ultrahigh speed 1050nm swept source / Fourier domain OCT retinal and anterior segment imaging at 100,000 to 400,000 axial scans per second, Optics Express, vol. 18, No. 19 (Sep. 13, 2010), pp. 20029-20048.
Werkmeister et al., Bidirectional Doppler Fourier-domain optical coherence tomography for measurement of absolute flow velocities in human retinal vessels, Optics Letters, vol. 33, Issue 24 (Dec. 15, 2008), pp. 2967-2969.
Zhao et al., Doppler standard deviation imaging for clinical monitoring of in vivo human skin blood flow, Optics Letters, vol. 25, No. 18 (Sep. 15, 2000), pp. 1358-1360.
Zotter et al., Visualization of microvasculature by dual-beam phase-resolved Doppler optical coherence tomography, Optics Express, vol. 19, No. 2 (Jan. 7, 2011), pp. 1217-1227.
European Extended Search Report dated Mar. 23, 2015, issued in European Patent Application No. 14306748.6, 6 pages.
Nicusor V. Iftimia, et al., Dual-beam Fourier domain optical Doppler tomography of zebrafish, Optics Express, Sep. 1, 2008, pp. 13624-13636, vol. 16, No. 18.

* cited by examiner

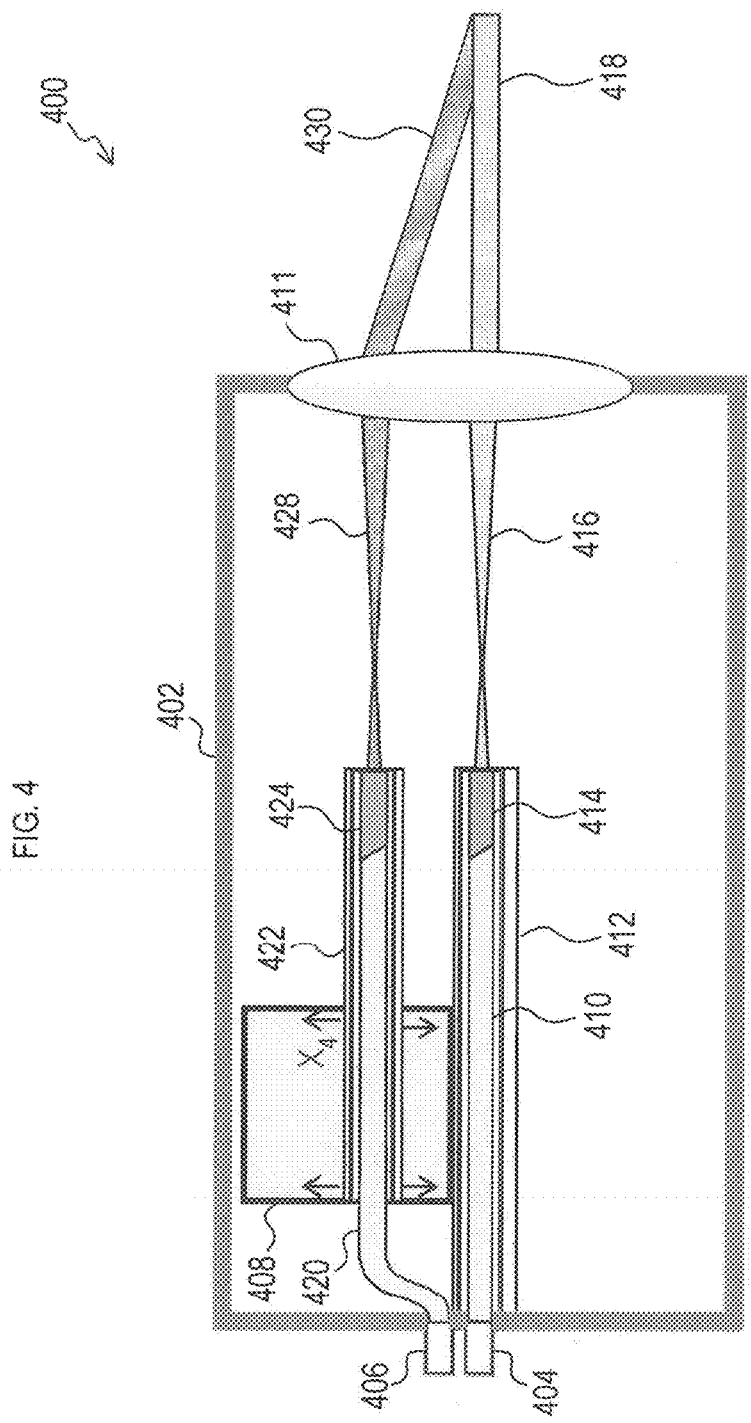

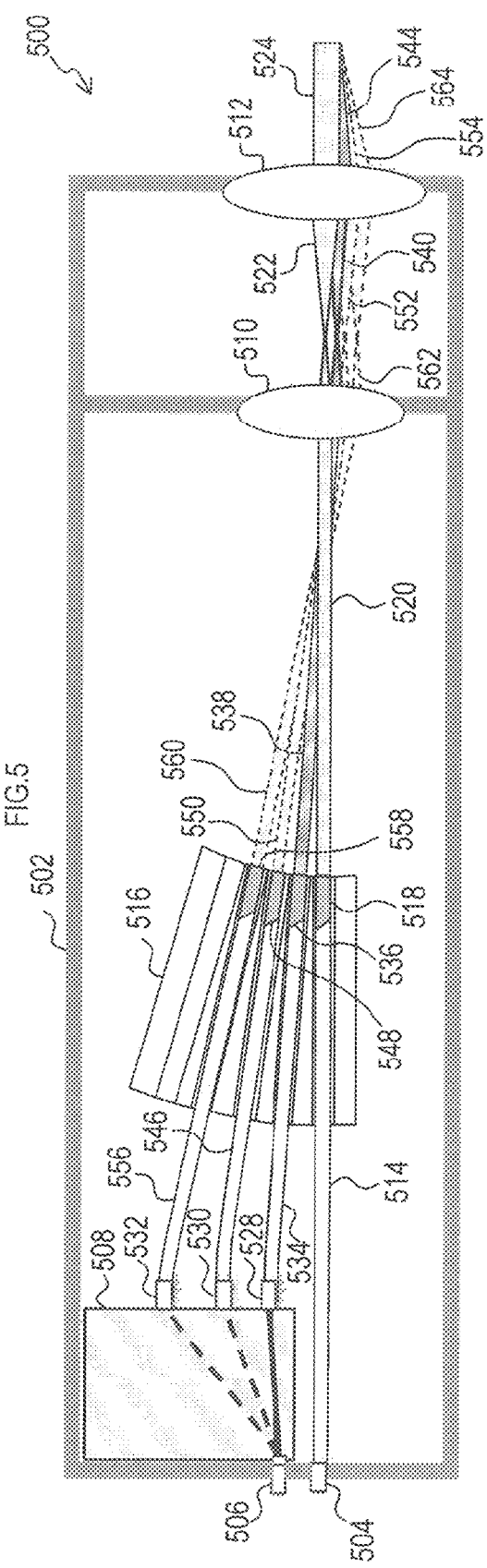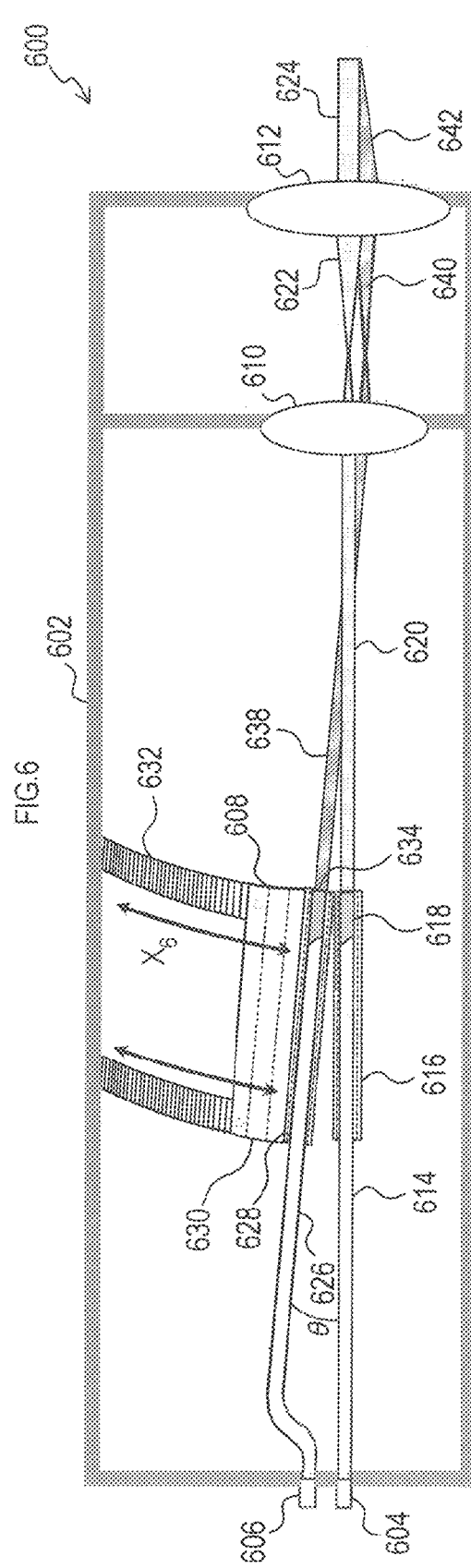

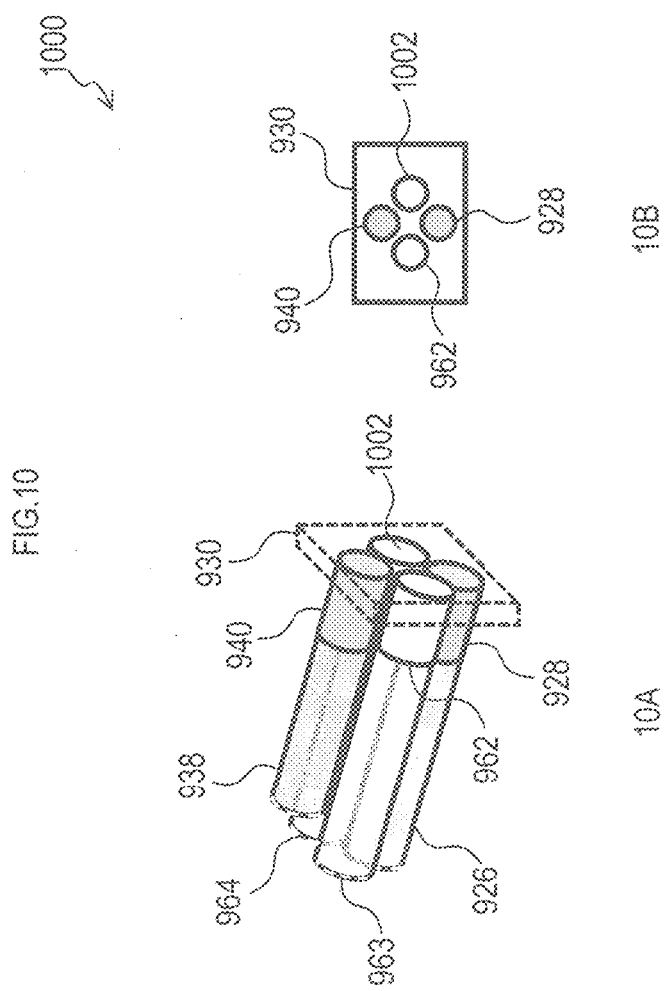

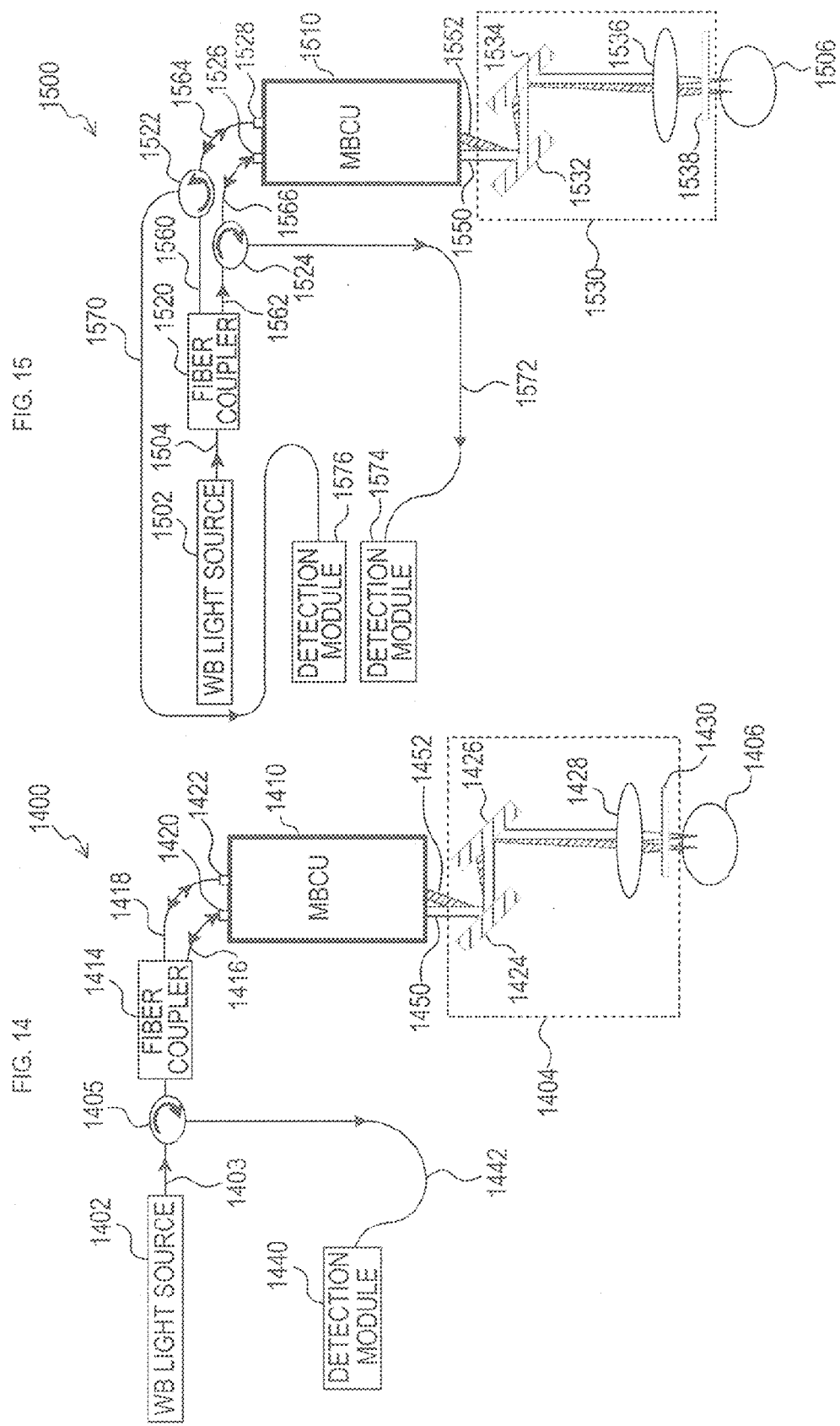

MULTI-CHANNEL OPTICAL COHERENCE TOMOGRAPHY

BACKGROUND

The present invention relates generally to the field of optical coherence tomography and, more particularly, to systems and methods for multi-channel optical coherence tomography.

Modern instrumental analysis techniques include sophisticated optical scanning at ever-greater resolutions. For example, the interferometric technique, optical coherence tomography ("OCT") provides three-dimensional images of scattering samples in the micrometer resolution range. Modern OCT techniques include swept-source OCT ("SS-OCT") and spectral-domain OCT ("SD-OCT"), which are commonly used in biomedical imaging systems. An exemplary SS-OCT approach is described by S. R. Chinn, et al. in "Optical coherence tomography using a frequency-tunable optical source," Opt. Lett., Vol. 22, Issue 5 (1997), pp. 340-342. An exemplary SD-OCT approach is described by A. F. Fercher, et al. in "Measurement of intraocular distances by backscattering spectral interferometry," Opt. Comm's, Vol. 117, Issues 1-2 (1995), pp. 43-48. For ease and brevity of explanation, the references cited herein are provided as citations. However, all references cited herein should be considered incorporated by reference in their entirety.

Broadly, both SS-OCT and SD-OCT generate a spectral interference signal between a reference signal and a sample signal using a low-coherence light source. In SS-OCT, the light source is swept in wavelength. In SD-OCT, the light source has a broadband spectrum. The spectral interference signal is a function of the wavelength of the light source illuminating the sample. The spectral interference signal Fourier transform amplitude gives the sample refractive index distribution along the sample depth, customarily referred to as the z-direction. Both SS-OCT and SD-OCT obtain volumetric data by scanning the sample surface along the fast lateral direction (customarily referred to as the x-direction) and the slow lateral direction (customarily referred to as the y-direction).

An additional technique, Doppler OCT, employs either SS-OCT or SD-OCT to determine the velocity of moving particles inside the sample, in addition to the structural image, by computing the phase difference of the OCT signal between two instants at a given location. One of ordinary skill in the art will understand that the maximum absolute value of the phase is $\pi$ and its minimum absolute value is limited by the phase noise, a result noted by B. H. Park, et al., in "Real-time fiber-based multi-functional spectral-domain optical coherence tomography at 1.3 µm," Opt. Express, Vol. 13, No. 11 (2005), pp. 3931-3944. One of ordinary skill in the art will also understand that the measurable velocity is proportional to the phase difference and inversely proportional to the time interval between the two measurements. Conventional Doppler OCT techniques, such as that presented in U.S. Pat. No. 6,549,801, execute phase difference measurements between adjacent lateral locations of the fast scanning direction (x-direction). An additional example is provided by Y. Zhao, et al., in "Doppler standard deviation imaging for clinical monitoring of in vivo human skin blood flow," Opt. Lett., Vol. 25, No. 18 (2000), pp. 1358-1360.

One of ordinary skill in the art will understand that measurement of adjacent lateral locations requires dense scanning in order to scan locations close enough together to return correlated OCT signals. This correlation requirement complicates the process of obtaining densely collected measurements. For example, ophthalmological and diagnostic applications commonly employ Doppler OCT to obtain motion information for retinal or choroidal blood vessels. However, typical modern in vivo ophthalmologic OCT measurements require a short volume acquisition time due to motion artifacts, power exposure limits, and other safety and environmental considerations.

Even with these limitations, recent developments in SS-OCT and SD-OCT have achieved scanning speeds over 400 kHz. Exemplary techniques are shown by T. Klein, et al., in "Megahertz OCT for ultrawide-field retinal imaging with a 1050 nm Fourier domain mode-locked laser," Opt. Express, Vol. 19, No. 4 (2011), pp. 3044-3062, by B. Potsaid et al., in "Ultrahigh speed 1050 nm swept source/Fourier domain OCT retinal and anterior segment imaging at 100,000 to 400,000 axial scans per second," Opt. Express, Vol. 18, No. 19 (2010), pp. 20029-20048, and by L. An, et al., in "Optical microangiography provides correlation between microstructure and microvasculature of optic nerve head in human subjects," J. Biomed. Opt., Vol. 17, No. 11 (2012), pp. 116018-1-116018-6.

A person of ordinary skill in the art will understand that SS-OCT Doppler measurements require accurate synchronization between the detected signal and the sweeping scan illuminations. One approach to this synchronization problem is to use a fiber Bragg grating, as described by H. C. Hendargo, et al. in "Doppler velocity detection limitations in spectrometer-based versus swept-source optical coherence tomography," Biomed. Opt. Express, Vol. 2, No. 8 (2011), pp. 2175-2188.

SS-OCT systems configured accordingly can be employed to obtain high-resolution volume information with a short time interval between adjacent sample point locations. So configured, standard Doppler OCT techniques can be employed to measure relatively fast motion occurring inside the sample. This approach has been used to measure blood flow near the optic nerve head in a human retina by W. Choi, et al., as described in "Phase-sensitive swept-source optical coherence tomography imaging of the human retina with a vertical cavity surface-emitting laser light source," Opt. Lett., Vol. 38, Issue 3 (2013), pp. 338-340.

However, this approach is less effective in measuring relatively slow motion occurring inside the sample. One of ordinary skill in the art will understand that sensitivity to slower motion within the sample ordinarily requires decreasing the time interval between phase measurements. One alternative approach is to modify the scanning protocol in the fast scanning direction (x-direction). Another alternative approach is to compute the phase difference between measurements along the slow scanning direction (y-direction), as proposed by B. Braaf, et al., in "Angiography of the retina and the choroid with phase-resolved OCT using interval-optimized backstitched B-scans," Opt. Express, Vol. 20, No. 18 (2012), pp. 20516-20534. These alternative approaches, however, fail to overcome the trade-off between spatial resolution (or scanning range size) and measurable velocity range. As such, several additional approaches have been proposed.

One such approach uses two spatially-separated probing beams. An exemplary expression of this approach is shown in U.S. Pat. Pub. No. 2012/0120408 A1. Generally, this approach scans a sample with two probing beams at the same speed, with a constant spatial shift between the two probing beams. In typical systems, this approach achieves improved motion sensitivity without excessive reduction in spatial resolution or lateral scanning range.

In a common dual-beam example, each probing beam scans the same location at different times. One probing beam (the "following" beam) scans the target location after a constant delay T with respect to the other probing beam (the "preceding" beam). For each target location, the phase of the preceding beam signal acquired at time t0 is compared with the phase of the following beam signal acquired at time t0+T. The common dual-beam approach allows for some measurement of relatively slower particle motions.

This approach has been successfully employed to obtain angiographies of the human choroid, as noted by F. Jaillon, et al., in "Variable velocity range imaging of the choroid with dual-beam optical coherence angiography," Opt. Express, Vol. 20, No. 1 (2012), pp. 385-396. Additionally, the measurable velocity range can be adjusted by modifying the delay, T, between the two probing beams, to optimize vessel contrast. As the delay, T, between the beams increases, slower motion can be measured. Different implementations of this technique have been demonstrated.

The original implementation of the common dual-beam technique used polarization multiplexing to generate the distinct probing beams, which introduced operational challenges and complexity. For example, the polarization multiplexing implementation requires the interferometer to use polarization-maintaining fibers and the probing arm to use a Wollaston prism or polarization beam splitter in order to separate the two beams.

As such, this implementation may be sensitive to the intrinsic birefringence of the probed sample, which reduces vessel contrast. This sensitivity to birefringence can be reduced somewhat by adding a Faraday rotator and a quarter waveplate in the probing arm, as described by M. Makita, et al., in "Dual-beam-scan Doppler optical coherence angiography for birefringence-artifact-free vasculature imaging," Opt. Express, Vol. 20, No. 3 (2012), pp. 2681-2692. However, this approach increases system complexity and cost.

Another implementation uses a second light source and combines the two probing beams with a non-polarizing beam splitter, as described by S. Zotter, et al., in "Visualization of microvasculature by dual-beam phase-resolved Doppler optical coherence tomography," Opt. Express, Vol 19, No. 2 (2011), pp. 1217-1227. This second implementation generates the two probing beams from a beam splitter and two independent light sources. One shortcoming of this implementation is that the beam splitter causes significant signal losses of the retinal backscattered signal. Additionally, this approach also increases system complexity and cost.

Another approach in some dual-beam systems is to employ two angularly separated probing beams. For example, such systems use two probing beams impinging on the same sample location at different angles. This approach is shown by, for example, R. Werkmeister, et al., in "Bidirectional Doppler Fourier-domain optical coherence tomography for measurement of absolute flow velocities in human retinal vessels," Opt. Lett., Vol. 33, Issue 24 (2008), pp. 2967-2969. Generally, this approach supports measuring the absolute velocity of motion inside the sample.

An early demonstration of application of this approach to laser Doppler velocimetry is presented in U.S. Pat. No. 5,900,928. Conventional Doppler OCT only determines the projection of the velocity direction over the probing beam direction or the axial velocity. Further, typical bidirectional dual-beam approaches can only determine absolute velocity under certain conditions. In particular, the typical approach requires that the plane defined by the two probing beams also contains the direction of the velocity vector under measurement. One approach to meeting this requirement is the rotation of the bulk optics to achieve alignment between the dual-beam plane and the desired velocity direction, as demonstrated by C. Blatter, et al., in "Dove prism based rotating dual beam bidirectional Doppler OCT," Biomed. Opt. Express, Vol. 4, No. 7 (2013), pp. 1188-1203. In this technique, alignment is achieved by rotating bulk optics, in particular a Dove prism, to measure blood velocity in the optic nerve head of the eye. One of ordinary skill in the art will appreciate that this technique tends to increase the cost and complexity of systems using this approach.

Therefore, there is a need for a system and/or method for optical coherence tomography that addresses at least some of the problems and disadvantages associated with conventional systems and methods.

SUMMARY

The following summary is provided to facilitate an understanding of some of the innovative features unique to the embodiments disclosed and is not intended to be a full description. A full appreciation of the various aspects of the embodiments can be gained by taking into consideration the entire specification, claims, drawings, and abstract as a whole.

An optical coherence tomography apparatus includes a multi-beam configuration unit comprising at least a first optical path having a first numerical aperture and a second optical path having a second numerical aperture. The multi-beam configuration unit orients the second optical path in a selected orientation in space relative to the first optical path. A scan system illuminates a sample with non-polarized light received from the multi-beam configuration unit and directs light returning from the sample to the first optical path and the second optical path. The multi-beam configuration unit directs light returning from the sample, along the first optical path and the second optical path, to an optical pathway leading to a processing system. The processing system performs optical coherence tomography motion analysis based on interference between light returning from the sample and a first reference signal.

In one embodiment, the multi-beam configuration unit receives a first sample beam and directs the first sample beam along the first optical path to the scan system. In one embodiment, the multi-beam configuration unit is further configured to receive a second sample beam and to direct the second sample beam along the second optical path to the scan system.

In one embodiment, the multi-beam configuration unit is further configured to orient the second optical path in a selected orientation in space relative to the first optical path by manipulation of optical components including one of the following: selecting one of a plurality of optical paths, wherein each optical path comprises a dedicated optical fiber; moving a first optical fiber in space relative to a second optical fiber; and moving a mirror to change the angle at which light from the first optical path intersects light from the second optical path.

In one embodiment, the multi-beam configuration unit is further configured to control the orientation of the first active beam to impinge upon a point on the scan system at a first angular displacement and to control the orientation of the second active beam to impinge upon the point on the scan system at a second angular displacement. The first active beam and the second active beam impinge upon the sample at locations separated by an interval based on the difference between the first angular displacement and the second angular displacement.

In one embodiment, the multi-beam configuration unit is further configured to control the orientation of the first active beam to impinge upon a first scan point on the scan system at a first location and to control the orientation of the second active beam to impinge upon a second scan point on the scan system at a second location; wherein the first location and the second location are separated by an interval; wherein the first active beam and the second active beam impinge upon the scan system in a parallel orientation in a first plane; wherein the first active beam impinges upon the sample at a sample point with a first angular displacement, the first angular displacement based on the first location; and wherein the second active beam impinges upon the sample at the sample point with a second angular displacement, the second angular displacement based on the second location.

In one embodiment, the multi-beam collimator is further configured to control the orientation of the first active beam to impinge upon a third scan point on the scan system at a third location and to control the orientation of the second active beam to impinge upon a fourth scan point on the scan system at a fourth location. The third location and the fourth location are separated by an interval. The first active beam, when oriented to illuminate the third scan point, and the second active beam, when oriented to illuminate the fourth scan point, impinge upon the scan system in a parallel orientation in a second plane, with the second plane perpendicular to the first plane.

In one embodiment, a reference arm couples to the multi-beam configuration unit and the processing system, the reference arm being configured to generate the first reference beam. In one embodiment, the scan module further comprises a partial reflector configured to reflect a portion of the first active beam and the second active beam, to generate a first reference signal, the first reference signal being one of the at least one reference signal.

In one embodiment, the processing system comprises a first detector configured to generate a first scan signal based on interference between a first part of light returning from the sample and the first reference signal. The processing system further comprises a second detector configured to generate a second scan signal based on interference between a second part of light returning from the sample and a second reference signal.

In one embodiment, the multi-beam configuration unit further comprises a third optical path, the multi-beam configuration unit being further configured to arrange the third optical path in a selected second orientation. The scanning module is further configured to scan the sample with the third active beam simultaneously with the first active beam and the second active beam.

An optical coherence tomography method includes orienting a first optical path in a selected orientation in space relative to a second optical path. The first optical path has a first numerical aperture and the second optical path has a second numerical aperture. The method includes illuminating a sample with non-polarized light and directing light returning from the sample, along the first optical path and the second optical path, to an optical pathway leading to a processing system. The processing system is configured to perform optical coherence tomography motion analysis based on interference between light returning from the sample and a first reference signal.

As described in more detail below, the above embodiments offer numerous technical advantages over typical systems and methods. For example, the embodiments described herein avoid the disadvantages associated with using polarization-maintaining fibers in the interferometer. Additionally, the embodiments described herein avoid the disadvantages associated with using a Wollaston prism or polarization beam splitter in the probing arm in order to generate the probing beams.

Additionally, the embodiments disclosed herein can be configured to improve the range of detectable velocities without also reducing spatial resolution or lateral scanning range. Moreover, the embodiments disclosed herein can be configured to improve motion sensitivity without excessive reduction in spatial resolution or lateral scanning range.

Furthermore, the embodiments disclosed herein can be configured to avoid or minimize the signal losses associated with a beam splitter, especially in the backscatter returning from the sample. The embodiments disclosed herein can also be configured to avoid requiring a Dove prism or otherwise having to rotate bulk optics to achieve absolute velocity measurement. Additionally, the embodiments disclosed herein can be configured to avoid excessive increases in cost or complexity, at least as compared with conventional techniques. One of ordinary skill in the art will be able to identify numerous other technical advantages, especially with respect to the embodiments described in more detail below.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 4 is a block diagram showing a multi-beam configuration unit in accordance with another embodiment;

FIG. 5 is a block diagram showing a multi-beam configuration unit in accordance with still another embodiment;

FIG. 6 is a block diagram showing a multi-beam configuration unit in accordance with yet another embodiment;

FIG. 10 is a block diagram showing an aspect of the multi-beam configuration unit of FIG. 9 in accordance with one embodiment;

FIG. 14 is a block diagram showing a multi-channel optical coherence tomography apparatus in accordance with still another embodiment;

FIG. 15 is a block diagram showing a multi-channel optical coherence tomography apparatus in accordance with yet another embodiment;

DESCRIPTION OF THE PREFERRED EMBODIMENT(S)

Figure 1:
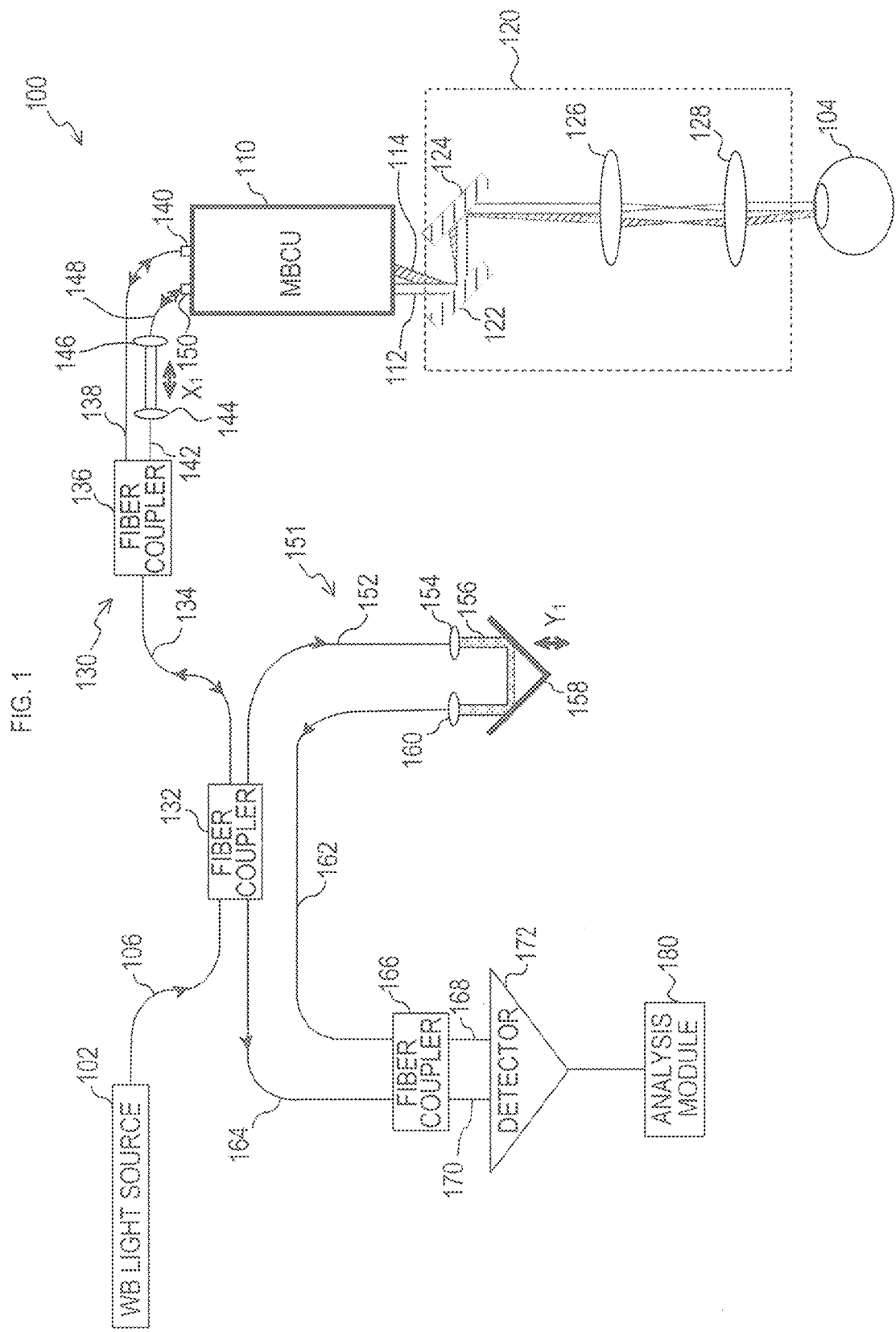
FIG. 1 is a block diagram showing a multi-channel optical coherence tomography apparatus in accordance with one embodiment.

The particular values and configurations discussed in these non-limiting examples can be varied and are cited merely to illustrate at least one embodiment and are not intended to limit the scope of the invention.

In the following discussion, numerous specific details are set forth to provide a thorough understanding of the present invention. Those skilled in the art will appreciate that the present invention may be practiced without such specific details. In other instances, well-known elements have been illustrated in schematic or block diagram form in order not to obscure the present invention in unnecessary detail. Additionally, for the most part, details concerning routine operations or devices such as light sources, fiber coupling techniques, optical scanning techniques, and the like, have been omitted inasmuch as such details are not considered necessary to obtain a complete understanding of the present invention, and are considered to be within the understanding of persons of ordinary skill in the relevant art.

Generally, the embodiments disclosed herein provide multi-beam OCT variants using an optical fiber-lens system that can simultaneously receive multiple beams of light returning from an illuminated sample, in order to measure the structure of, and motion inside, the sample. Broadly, the embodiments disclosed herein operate with beams of illuminating light, or returning light pathways, that are either spatially or angularly separated, as described in more detail below. Additionally, as described in more detail below, the various embodiments disclosed herein can be configured to perform either SD-OCT or SS-OCT, with appropriate modifications as will be understood by one having ordinary skill in the art.

Generally, the disclosed embodiments of the present invention can be classified into one of two aspects. The first aspect, in several embodiments, uses a fiber lens array associated with micro-lenses in order to produce small distances between contemporaneous active beams on the sample. One having ordinary skill in the art will understand that smaller distances between scanning beams allows measurement of faster motion inside the sample. That is, in the first aspect, spatial separation between active beams translates into a delay between scans of the same physical location on the sample. In the first aspect, the spatial separation, and therefore the delay, can be varied. This variability provides for improved Doppler OCT, with the flexibility of adjusting the measurable axial velocity ranges without changing the scan protocol, in either the scanning density or scanning range, for example.

The second aspect, in several embodiments, uses a fiber lens array associated with micro-lenses in order to produce active beams that contemporaneously impinge on the sample at the same location, with different angles of incidence. One having ordinary skill in the art will understand that this configuration, as described in more detail below, can be manipulated to measure the absolute velocity of motion inside the sample.

For the most part, the embodiments of the two aspects described herein are described in terms of two (or more) active beams, either spatially or angularly separated on the sample. One of ordinary skill in the art will understand that the categorization of a particular embodiment into one aspect or the other is not limiting. Moreover, in some embodiments, especially in embodiments with single beams, it is the return paths that are either spatially or angularly separated on the sample. That is, one of ordinary skill in the art will understand that the embodiments disclosed herein can be configured to receive returning light from a sample along spatially or angularly separated beam pathways, even though only a single active beam illuminates the sample.

One of ordinary skill in the art will understand that sample birefringence artifacts decrease the Doppler contrast originating from motion inside the sample. In retina imaging, for example, and especially in choroidal angiographies near the optic nerve head, the birefringence of the sclera will decrease the Doppler contrast of choroidal vessels. As such, one of ordinary skill in the art will understand that active polarization multiplexing is vulnerable to sample birefringence, which degrades the returning Doppler OCT signals. In the illustrated embodiments of the present invention, the light beams used to illuminate the sample (sometimes referred to herein as the "active beams," "scanning beams," "probing beams," or "sample beams") are generated without polarization multiplexing. As described in more detail below, avoiding polarization multiplexing reduces contrast degradation due to sample intrinsic birefringence.

Furthermore, the embodiments of the present invention described herein do not employ a bulk non-polarizing beam splitter to split the light into active beams. Using a non-polarizing beam splitter usually implies significant light loss from the beam splitter. As such, the embodiments described herein avoid using a bulk beam splitter and therefore reduce signal degradation due to losses in the device used to generate the multiple active beams.

Figure 20:
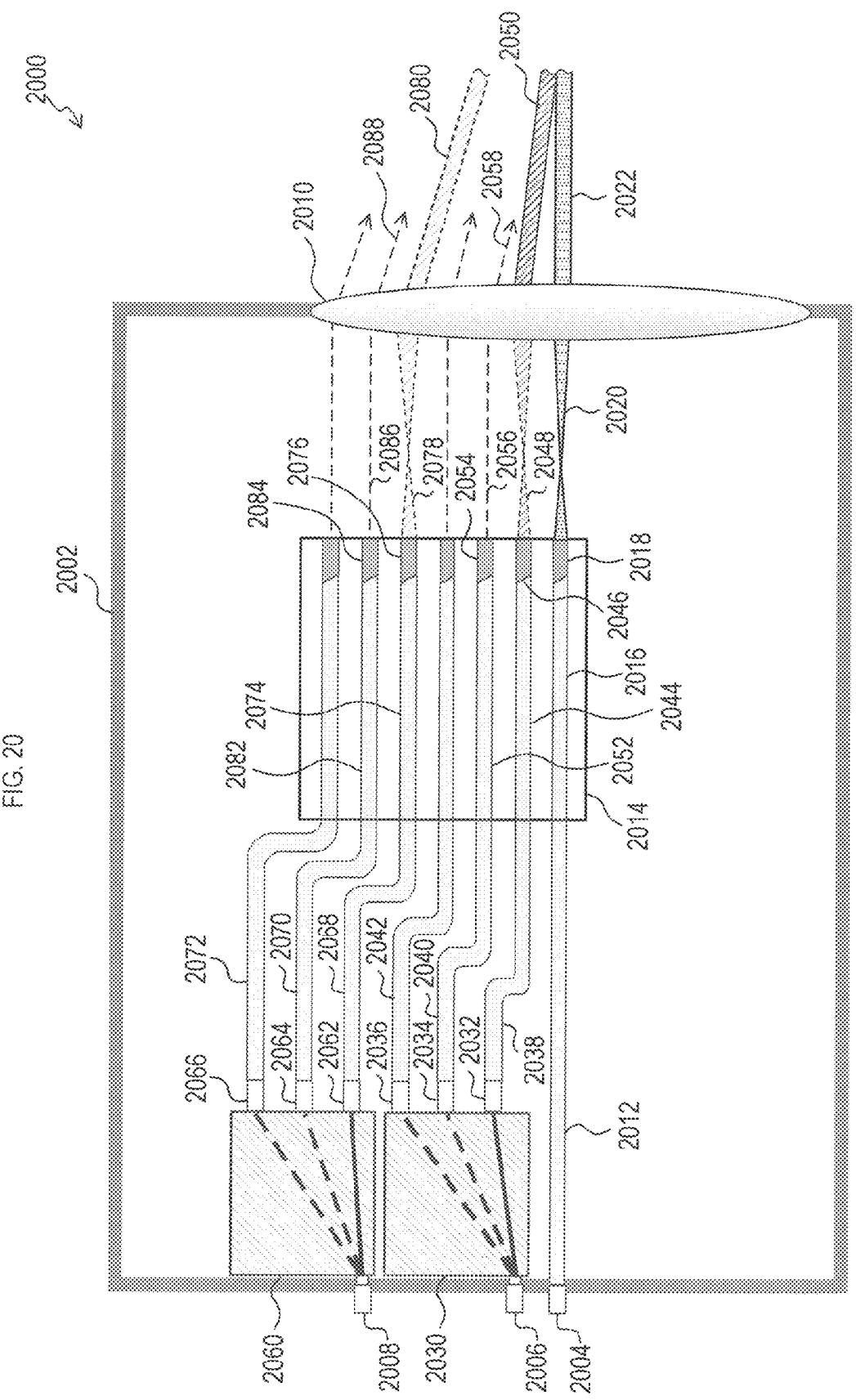
FIG. 20 is a block diagram showing a multi-beam configuration unit and a scan system in accordance with yet another embodiment.

Additionally, the disclosed embodiments are mostly described with respect to embodiments employing two active beams, in order to simplify the description. However, one having ordinary skill in the art, using the principles described herein, will understand how to configure systems with more than two simultaneous probing beams. FIG. 20 provides an example of one such system.

Turning now to various specific embodiments, FIG. 1 is a block diagram showing a multi-channel optical coherence tomography apparatus in accordance with one embodiment. More specifically, FIG. 1 is a high-level block diagram illustrating certain components of a system 100 for multi-channel optical coherence tomography, in accordance with a preferred embodiment of the present invention. Generally, as used herein, a "multi-channel" system is a multi-beam system that captures light returning from an illuminated sample along two or more optical paths. In the illustrated embodiment, system 100 includes a wideband (WB) light source 102, a multi-beam configuration unit (MBCU) 110, a scan system 120, a sample arm 130, and a reference arm 151.

Generally, WB light source 102 is an otherwise conventional light source that generates wideband source light. In the illustrated embodiment, source 102 couples to the sample arm 130 and the reference arm 151. In the illustrated embodiment, light in the sample arm 130 is further coupled into two separate active beams that are routed through the MBCU 110 and scan system 120 to impinge upon and then reflect from the sample 104.

Generally, some of the light impinging upon sample 104 is reflected as backscatter, a portion of which returns from sample 104 along the paths taken by the active beams illuminating sample 104. Light returning from sample 104 returns through the scan system 120 and MBCU 110, and sample arm 130. Additionally, reference arm 151 generates a reference signal for use in calculating volume and motion information about the sample. In the illustrated embodiment, a single detector is employed. One of ordinary skill in the art will appreciate that systems with more than one detector can also be employed. Some exemplary multi-detector systems are described below. In the illustrated embodiment, system 100 is configured for SS-OCT. In the following descriptions, one having ordinary skill in the art will understand that systems that allow the synchronization between the light source, the scanning system, the optical switch, and the detection have been omitted for ease of discussion.

More particularly, in the illustrated embodiment, source 102 couples to an otherwise conventional single mode fiber 106. Source 102 generates wideband, swept-source light, which passes through fiber 106 to a fiber coupler 132. Fiber coupler 132 is an otherwise conventional 2×2 fiber coupler. Light entering fiber coupler 132 from fiber 106 passes to sample arm 130, through an otherwise conventional single mode fiber 134, and to reference arm 151, through an otherwise conventional single mode fiber 152.

In the illustrated embodiment, light passing from fiber coupler 132 along fiber 134 enters fiber coupler 136. Fiber coupler 136 is an otherwise conventional 1×2 fiber coupler. Light entering fiber coupler 136 from fiber 134 passes to an otherwise conventional single mode fiber 138 and an otherwise conventional single mode fiber 142. Light entering fiber 138 from fiber coupler 136 enters MBCU 110 at an entry port 140. One of ordinary skill in the art will understand that the length of fiber 138 presents an optical path of a particular length.

Light entering fiber 142 from fiber coupler 136 enters a collimator lens 144 followed by a condensing lens 146. In the illustrated embodiment, collimator lens 144 is an otherwise conventional collimator lens and condensing lens 146 is an otherwise conventional condensing lens. One of ordinary skill in the art will understand that suitable substitute optics can also be employed. In the illustrated embodiment, condensing lens 146 couples to an otherwise conventional single-mode fiber 148, which delivers light exiting condensing lens 146 to MBCU 110 at an entry port 150.

In the illustrated embodiment, collimator lens 144 and condensing lens 146 are separated by a configurable distance, represented by the arrow "$X_1$". In the illustrated embodiment, the path length between fiber 142 and fiber 148 can be adjusted by configuring the distance $X_1$ to a desired distance. One of ordinary skill in the art will appreciate that the specific distance $X_1$ determines a relative delay between light travelling along fiber 138 and light travelling along fiber 142 and fiber 148. One of ordinary skill in the art will also appreciate that this approach can be replaced with any other suitable, well-known mechanism to vary the path length between fiber 142 and fiber 148, in order to provide a path length that differs from the path length of fiber 138 by a desired amount.

As described in more detail below, light entering MBCU 110 at port 140 and port 150 is configured by MBCU 110 to generate active beams 112 and 114. Generally, light entering port 150 from fiber 148 exits MBCU 110 as a scanning beam 112. Similarly, light entering port 140 from fiber 138 exits MBCU 110 as a scanning beam 114. As described in more detail below, beam 112 and beam 114 are separated by an angle configured by MBCU 110.

In the illustrated embodiment, beam 112 and beam 114 enter scan system 120, which manipulates the beams according to a selected scanning protocol to scan sample 104. Generally, scan system 120 is configured to illuminate a sample with non-polarized light received from MBCU 110, and to direct light returning from sample 104 to the first optical path and the second optical path of MBCU 110. One of ordinary skill in the art will understand that any of a variety of well-known scanning protocols can be employed.

In the illustrated embodiment, scan system 120 includes a scanning mirror 122, a scanning mirror 124, a lens 126, and a lens 128. Scanning mirrors 122 and 124 are otherwise conventional scanning mirrors and lenses 126 and 128 are otherwise conventional lenses used in scan systems. In the illustrated embodiment, scan system 120 is shown with two lenses, lenses 126 and 128. In an alternate embodiment, depending on the sample, lens 128 can be omitted. One of ordinary skill in the art will understand that other lens combinations can be employed. For ease of illustration, various control elements and structural support frameworks have been omitted. One of ordinary skill in the art will understand that these omitted elements are standard in conventional scan systems and can be readily adapted for use in the disclosed embodiments.

Generally, beam 112 and beam 114 are reflected from scanning mirror 122 to scanning mirror 124. Scanning mirror 124 reflects beams 112 and 114 through lenses 126 and 128. In the illustrated embodiment, the sample 104 is not directly accessible. For example, in one embodiment sample 104 is a human eye and the desired surface is the retina. As such, one of ordinary skill in the art will understand that such imaging requires the conjugate of the scanning system to be positioned at the pupil. In an alternate embodiment, in cases where the sample 104 is directly accessible, such as the case where sample 104 is a human cornea, for example, lens 128 can be omitted. In such cases, system 100 or sample 104 is arranged so that sample 104 is positioned in the focal plane of lens 126.

Beams 112 and 114 leave scan system 120 and impinge upon sample 104. One of ordinary skill in the art will appreciate that the selected scanning protocol will manipulate mirrors 122 and 124 to scan sample 104, which simultaneously displaces beams 112 and 114 by the same displacement amount. Sample 104 absorbs some of the light from beams 112 and 114 and back-reflects some of the light from beams 112 and 114 along the same path beams 112 and 114 traveled to reach sample 104. In the illustrated embodiment, the light returning back-reflected from sample 104 travels through lens 128, then lens 126, to mirror 124 and mirror 122, into MBCU 110.

Thus, light from beam 112 reflected by sample 104 couples from MBCU 110 at port 150 into fiber 148. Similarly, light from beam 114 reflected by sample 104 couples from MBCU 110 at port 140 into fiber 138. The returning light in fibers 138 and 148 return to fiber coupler 136. As in the forward direction, the light returning along fiber 148 experiences a delay between lenses 146 and 144, with respect to the light returning along fiber 138. As used herein, the light returning to fiber coupler 136 along fibers 148 and 142 is sometimes referred to as "delayed light" in the sample arm. Similarly, as used herein, the light returning to fiber coupler 136 along fiber 138 is sometimes referred to as "non-delayed" light. Additionally, as described above, lenses 144 and 146 are illustrative of a wide variety of well-known alternative mechanisms for introducing delay between optical paths, which will be readily understood by one of ordinary skill in the art.

In the illustrated embodiment, light returning from sample 104 along fibers 138 and 142 is recoupled in fiber coupler 136. Fiber coupler 136 directs the re-coupled light back along fiber 134, which delivers the recoupled light back to fiber coupler 132. Fiber coupler 132 delivers the recoupled light to an otherwise conventional single mode fiber 164, which, in turn, delivers the recoupled light to an otherwise conventional fiber coupler 166.

As described above, fiber coupler 132 also couples light from source 102 to reference arm 151. In particular, in the illustrated embodiment, fiber coupler 132 couples light from source 102 to an otherwise conventional single mode fiber 152. In the illustrated embodiment, fiber 152 couples received light to an otherwise conventional collimator lens 154.

In the illustrated embodiment, collimator lens 154 generates a reference beam 156, which leaves lens 154 to impinge upon a mirror 158. In the illustrated embodiment, mirror 158 comprises two reflective surfaces that are arranged at a 90 degree angle to each other. Additionally, the distance between mirror 158 and lens 154 can be adjusted by positioning mirror 158 along the direction indicated by arrow $Y_1$. Thus, one of ordinary skill in the art will appreciate that by translating mirror 158, the reference arm optical path length can be adjusted. One of ordinary skill in the art will also appreciate that other well-known reference techniques can also be employed. For example, in one embodiment, an adjustable path length can be substituted for lens 154, mirror 158, and lens 160, as will be understood by one of ordinary skill in the art. Additionally, alternative reference techniques consistent with the present invention are described below.

In the illustrated embodiment, mirror 158 reflects beam 156 to an otherwise conventional condensing lens 160. Condensing lens 160 couples the reference light from beam 156 to an otherwise conventional single-mode fiber 162, which delivers the light to fiber coupler 166. As used herein, light from reference arm 151 is sometimes referred to as a "reference signal" or "reference beam." In the illustrated embodiment, fiber coupler 166 is an otherwise conventional 2×2 fiber coupler. In the illustrated embodiment, fiber coupler 166 couples the delayed and non-delayed light returning from sample arm 130 and the reference light from reference arm 151. Light returning from sample arm 130 interferes with light from reference arm 151 and fiber coupler 166 generates interference signals that are coupled to otherwise conventional single mode fibers 168 and 170.

In the illustrated embodiment, fibers 168 and 170 deliver the interference signals to a detector 172. In the illustrated embodiment, detector 172 is an otherwise conventional balanced photo-detector. One of ordinary skill in the art will understand that other suitable detectors can also be employed. In the illustrated embodiment, detector 172 generates a scan signal based on the received interference signals. In one embodiment, the scan signal is an otherwise conventional output of an otherwise conventional optical detector. In an alternate embodiment, the scan signal can be configured based on the requirements of the system or systems that will use the scan signal.

In the illustrated embodiment, detector 172 delivers the scan signal to an analysis module 180. Generally, analysis module 180 is configured to filter, amplify, digitize, and otherwise process the scan signal to obtain volumetric, structural, and/or motion information about sample 104, as described in more detail below. In one embodiment, analysis module 180 is a computer system configured to process scan signal 180.

In one embodiment, detector 172 and analysis module 180 together comprise a processing system. In an alternate embodiment, detector 172, analysis module 180, and fiber coupler 166 together comprise a processing system. Generally, as used herein, a "processing system" is a collection of one or more components configured to perform optical coherence tomography analysis based on received input. In one embodiment, a processing system is configured to perform optical coherence tomography motion analysis, which one of ordinary skill in the art will understand to be analysis of the velocity (relative or absolute) of particles inside the sample. In one embodiment, a processing system is further configured to perform volumetric or structural analysis, which one of ordinary skill in the art will understand to be analysis of the physical structure and/or volume of the sample.

In the illustrated embodiment, system 100 is configured with a single detector, detector 172. As such, one of ordinary skill in the art will understand that, for each scan position on the sample, two signals are acquired, one from each of the two scanning beams. Therefore, for a given depth OCT profile containing structure and phase information, the two acquired signals (i.e., light returning along two different paths from the sample) are separated by a delay equal to the optical path-length difference between paths of the two acquired signals. One of ordinary skill in the art will understand that this configuration is suitable in cases where the desired depth range of the detection is large enough to contain both signals. So configured, one of ordinary skill in the art will understand that the phase difference between the delayed and non-delayed OCT signals can be computed, and the Doppler shift calculated, at each sample position to obtain motion information about the sample.

Figure 2:
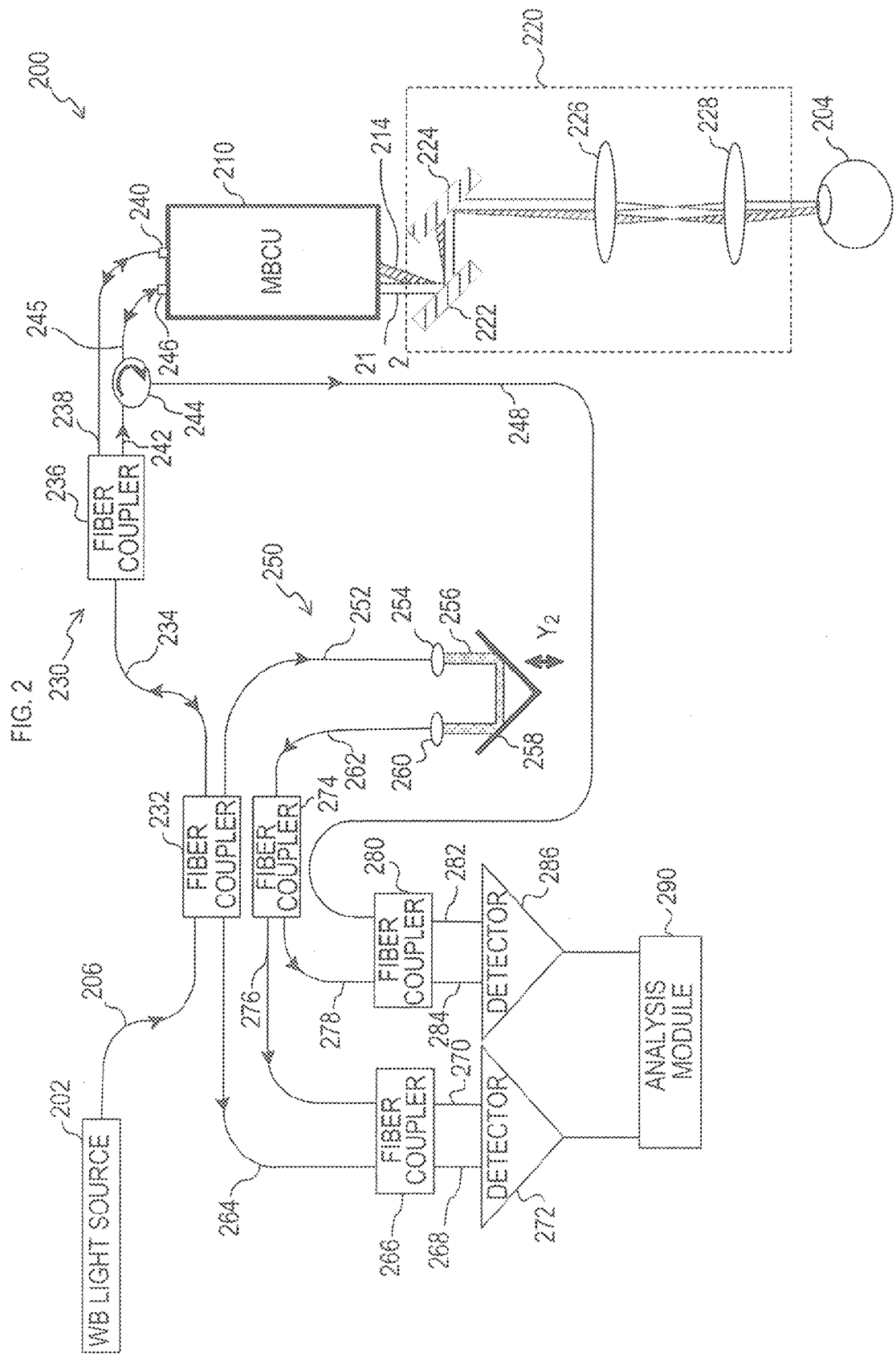
FIG. 2 is a block diagram showing a multi-channel optical coherence tomography apparatus in accordance with another embodiment.

The embodiment illustrated in FIG. 1 uses a single detector. In an alternate embodiment, multiple detectors can also be employed. For example, FIG. 2 is a block diagram showing a multi-channel optical coherence tomography apparatus in accordance with a two-detector embodiment. Specifically, FIG. 2 shows a multi-channel OCT system 200 that includes a wideband (WB) light source 202, a multi-beam configuration unit (MBCU) 210, a scan system 220, a sample arm 230, and a reference arm 250. One of ordinary skill in the art will understand that system 200 operates on similar principles as those of system 100, modified as described herein.

For example, generally, WB light source 202 is an otherwise conventional light source that generates wideband source light, which is coupled to otherwise conventional single mode fiber 206. Fiber 206 delivers light from source 202 to an otherwise conventional 2×2 fiber coupler 232. Light entering fiber coupler 232 from fiber 206 passes to sample arm 230, through an otherwise conventional single mode fiber 234, and to reference arm 250, through an otherwise conventional single mode fiber 252.

In the illustrated embodiment, light passing from fiber coupler 232 along fiber 234 enters otherwise conventional 1×2 fiber coupler 236. Light entering fiber coupler 236 from fiber 234 passes to an otherwise conventional single mode fiber 238 into an entry port 240 of MBCU 210.

Light entering fiber coupler 236 from fiber 234 passes to an otherwise conventional single mode fiber 242 into a bi-directional transmitter 244. In the illustrated embodiment, bi-directional transmitter 244 is an otherwise conventional optical circulator. In an alternate embodiment, other suitable equivalents can also be employed. One of ordinary skill in the art will understand that in the illustrated configuration, light from single mode fiber 242 passes through transmitter 244 into otherwise conventional single mode fiber 245, and then into MBCU 210 at an entry port 246.

As described in more detail below, light entering MBCU 210 at port 240 and port 246 is configured by MBCU 210 to generate active beams 214 and 212, respectively. In the illustrated embodiment, beams 212 and 214 enter scan system 220, which manipulates the beams according to a selected scanning protocol to scan sample 204. In the illustrated embodiment, scan system 220 includes a scanning mirror 222, a scanning mirror 224, a lens 226, and a lens 228.

Beams 212 and 214 leave scan system 220 and impinge upon sample 204, generating light that reflects back through scan system 220 and MBCU 210 along the paths taken by beams 212 and 214. In the illustrated embodiment, light from beam 212 reflected by sample 204 couples from MBCU 210 at port 246 into fiber 245. Similarly, light from beam 214 reflected by sample 204 couples from MBCU 210 at port 240 into fiber 238. The returning light in fiber 238 returns to fiber coupler 236.

In the illustrated embodiment, light returning from sample 204 along fiber 238 passes through fiber coupler 236 and fiber 234 to fiber coupler 232. Fiber coupler 232 delivers the returning light to an otherwise conventional single mode fiber 264, which, in turn, delivers the recoupled light to an otherwise conventional fiber coupler 266.

In contrast with the embodiment described with respect to FIG. 1, system 200 does not implement a delay between the active beams. Instead of the adjustable delay generated between lenses 144 and 146 of FIG. 1, system 200 uses bi-directional transmitter 244. In one embodiment, the length of fiber 242 can be adjusted in order to reduce or avoid cross-talk errors at the detection. Light returning from sample 204 along fiber 245 is redirected by transmitter 244 and otherwise conventional single mode fiber 248 to an otherwise conventional 2×2 fiber coupler 280.

As described above, fiber coupler 232 also couples light from source 202 to reference arm 250, in a similar fashion as in system 100 of FIG. 1. In particular, in the illustrated embodiment, fiber coupler 232 couples light from source 202 to an otherwise conventional single mode fiber 252. Fiber 252 couples received light to an otherwise conventional collimator lens 254, which generates a reference beam 256, which leaves lens 254 to impinge upon a mirror 258 (adjustable along the direction indicated by arrow $Y_2$), reflecting light into an otherwise conventional condensing lens 260. Condensing lens 260 couples the reference light from beam 256 to an otherwise conventional single-mode fiber 262, which delivers the light as a reference beam to otherwise conventional 1×2 fiber coupler 274. Fiber coupler 274 delivers the reference beam to otherwise conventional fibers 276 and 278.

Fiber coupler 266 couples the light from fiber 264 and the reference beam in fiber 276 to generate a first interference signal, which fiber coupler 266 delivers to an otherwise conventional detector 272, via fibers 268 and 270. Similarly, fiber coupler 280 couples the light from fiber 248 and the reference beam in fiber 278 to generate a second interference signal, which fiber coupler 280 delivers to an otherwise conventional detector 286, via fibers 282 and 284.

In the illustrated embodiment, detector 272 generates a first scan signal based on the received first interference signal and delivers the first scan signal to analysis module 290. Similarly, detector 286 generates a second scan signal based on the received second interference signal and delivers the second scan signal to analysis module 290. Generally, analysis module 290 is configured to filter, amplify, digitize, and otherwise process the first and second scan signals to obtain volumetric, structural, and/or motion information about sample 204, as described in more detail below.

One having ordinary skill in the art will understand that the configuration of system 200 separately detects the interference signals based on the independent active beams and, therefore, system 200 can operate over a larger depth range than, for example, system 100. As configured in system 200, for each voxel, two OCT signals are acquired, and phase difference between the acquired OCT signals can be computed and Doppler shift calculated at each sample location.

One having ordinary skill in the art will understand that system 100 and system 200 can be readily configured for SD-OCT analysis. For example, in one embodiment, based on system 200, source 202 is a super luminescent diode (SLD). In one embodiment, system 200 replaces each of the 2×2 fiber couplers 266 and 280 with a 1×2 fiber, each of which is configured with two inputs (the reference beam and light returning from the sample) and one output to the associated detector. In one embodiment, system 200 replaces each of the detectors 286 and 272 with a spectrometer.

As described above, system 100 and system 200 provide active beams from an MBCU 110, 210 to a scan system 120, 220. FIGS. 3-7 and 20 illustrate various embodiments of a multi-beam configuration unit. Generally, each of these disclosed MBCUs is configured to generate two (or more) output collimated scanning beams that will intersect on the pivot point of the scanning system. One having ordinary skill in the art will understand that this configuration generates two beams impinging onto the sample at different locations, with the same incident angle. As such, these figures illustrate embodiments using spatially separated sample beams. One having ordinary skill in the art will understand that this configuration allows contrasting motions inside the sample according to their axial velocity ranges by changing beam distance on the sample.

Additionally, in some embodiments, one or more elements depicted as separate from the MBCU can instead be incorporated into the MBCU. For example, in an alternate embodiment, fiber 234 couples to MBCU 210 and MBCU 210 includes fiber coupler 236, fibers 238, 242, 245, and transmitter 244.

Furthermore, in the illustrated embodiments, the MBCU, such as MBCU 110/210 of FIGS. 1 and 2, for example, is configured to direct light returning from the sample along a first and second optical path inside the MBCU to an optical pathway leading to a processing system. Generally, an MBCU is configured to direct light returning from the sample to an optical pathway leading to a processing system when the optical pathway is configured to direct light returning from the sample to a component or components that can process the light, whether as light (such as in a fiber coupler) or as an interference signal (such as in detector or spectrometer).

One of ordinary skill in the art will understand that the particular components that comprise the optical pathway will depend on the particular configuration of the overall system, in most cases. In the case of MBCU 210, for example, one optical pathway (comprising fibers 238, 234, 264 and fiber couplers 236, 232, 266) leads to a processing system comprising detector 272 and analysis module 290. As described above, analysis module 290 performs optical coherence tomography motion analysis based on an interference signal from detector 272, which generates the interference signal based on interference (occurring in fiber coupler 266) between light returning from the sample (from fiber 264) and a reference signal (light from fiber 276).

Similarly, a second optical pathway (comprising fibers 245, 248 and transmitter 244) leads to a processing system comprising fiber coupler 280, detector 286, and analysis module 290. As described above, analysis module 290 performs optical coherence tomography motion analysis based on an interference signal from detector 286, which generates the interference signal based on interference (occurring in fiber coupler 280) between light returning from the sample (from fiber 248) and a reference signal (light from fiber 278). In each case, MBCU 210 directs light returning from sample 204 along an (internal) optical path that couples the returning light to an optical pathway that, in turn, delivers the light to a component or components configured to perform optical coherence tomography motion analysis based on interference between light returning from the sample and a reference signal.

Figure 3:
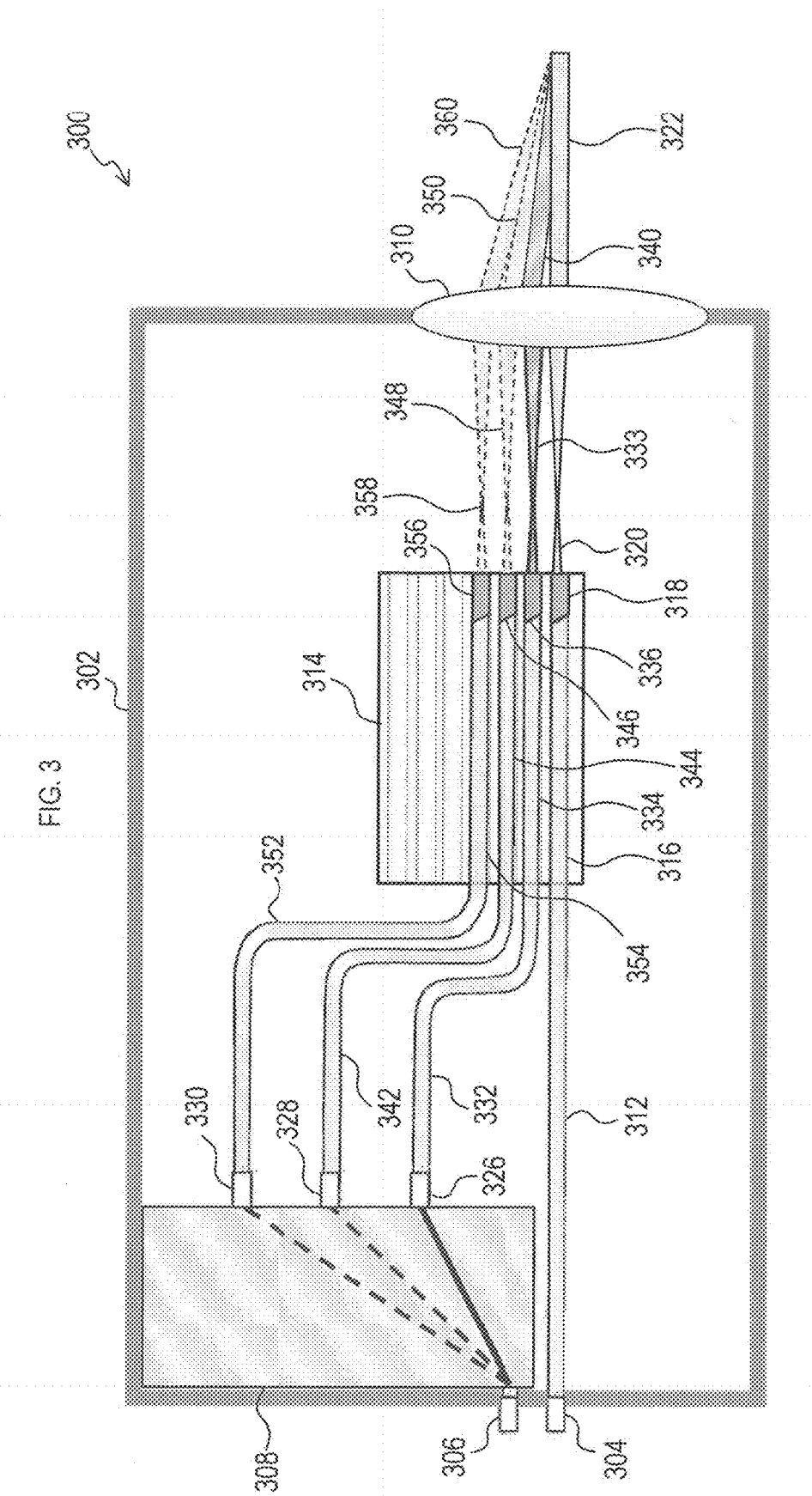
FIG. 3 is a block diagram showing a multi-beam configuration unit in accordance with one embodiment.

FIG. 3 is a block diagram showing a multi-beam configuration unit in accordance with one embodiment. More particularly, FIG. 3 illustrates an MBCU 300 configured with an optical switch, a plurality of optical fibers and tip lenses, and an exit lens. In the illustrated embodiment, MBCU 300 includes a frame 302, configured to provide a structure to which one or more of the various components of MBCU 300 can be fixed in a static orientation and/or position in space. In an alternate embodiment, frame 302 can be omitted. In an alternate embodiment, one or more components of MBCU 300 can be configured outside frame 302. One of ordinary skill in the art will understand that other configurations can also be employed.

MBCU 300 includes input ports 304 and 306, which couple to frame 302. Generally, input ports 304 and 306 are each configured to couple an optical fiber to the components of MBCU 300, as described in more detail below. In operation, input ports 304 and 306 receive input light, which is passed through to an exit lens 310 as scanning beams having a desired orientation in space relative to each other. In one embodiment, MBCU 300 is configured to generate two collimated beams 322 and 340 having a minimum angle of the order of 0.1 degree.

In the illustrated embodiment, input port 304 couples received light to an otherwise conventional single mode fiber 312. A plate 314 holds fiber 312 in a fixed orientation relative to exit lens 310. In the illustrated embodiment, plate 314 is an otherwise conventional V-groove plate. One of ordinary skill in the art will understand that other suitable mechanisms can be employed to hold fiber 312 in a fixed orientation.

In the illustrated embodiment, the surface tip of fiber 312 is shown with an angle configured to reduce back-reflections. In an alternate embodiment, fiber 312 can be configured without this angle. In the illustrated embodiment, the surface tip of fiber 312 couples to a tip lens 318. As used herein, a "tip lens" is an optical device configured to operate with a desired numerical aperture. In the illustrated embodiment, tip lens 318 is an otherwise conventional gradient refractive index (GRIN) micro lens. One of ordinary skill in the art will understand that the tip lens can also be configured as a sculpted fiber portion of fiber 312, a micro-lens, a micro-GRIN lens, a micro-lens array, a plano-convex micro-lens array, or other suitable optical device. One having ordinary skill in the art will understand that a micro-lens (or similar lens) can be substituted with a suitably small less, such as a 1 mm lens, for example.

Generally, tip lens 318 is configured to obtain the desired focusing or diverging property for beam 323. In one embodiment, tip lens 318 is configured to provide a desired numerical aperture. In one embodiment, tip lens 318 is configured to provide a desired divergence. In one embodiment, tip lens 318 includes a coating configured to reduce back-reflections.

In the illustrated embodiment, fiber 312 and tip lens 318 are co-axial and have equal or similar outer diameters. For example, in one embodiment values of the outer diameter are in the range of about 125 μm to 250 μm. In the illustrated embodiment, output beam 320 of tip lens 318 impinges upon exit lens 310 at or near the center of exit lens 310. In the illustrated embodiment, the resultant beam, output beam 322, is collimated. Generally, fiber 312 and tip lens 318 together comprise an optical path of MBCU 300.

In the illustrated embodiment, input port 306 is configured to couple received input light to an otherwise conventional optical switch 308. In the illustrated embodiment, optical switch 308 is configured to direct received light to one of three ports 326, 328, and 330. One of ordinary skill in the art will understand that configurations having more or less than three ports can also be employed. Generally, each of optical ports 326, 328, and 330 are configured to route received light along a path having a particular orientation in space relative to the path of optical fiber 312.

In the illustrated embodiment, ports 330, 328, and 326 are coupled to otherwise conventional single mode fibers 352, 342, and 332, respectively. Fibers 352, 342, and 332 are coupled to tip lenses 356, 346, and 336, respectively. In the illustrated embodiment, each of fibers 352, 342, and 332 (and their associated tip lenses) are held in a fixed orientation by plate 314. In the illustrated embodiment, plate 314 aligns fibers 352, 342, and 332 parallel to each other and to fiber 312. In the illustrated embodiment, plate 314 secures fibers 312, 332, 342, and 352 within grooves 316, 334, 344, and 354, respectively. In one embodiment, the minimum inter-fiber distance corresponds to approximately the lens diameter of the tip lenses. One of ordinary skill in the art will understand that other configurations can also be employed.

So configured, optical switch 308 can be operated to direct incoming light along one of fibers 352, 342, and 332, thereby selecting one of beams 358, 348, and 333, respectively. In the illustrated embodiment, beam 333 has been selected. Each of beams 358, 348, and 333 impinge on exit lens 310, generating beams 360, 350, and 340, respectively. Generally, exit lens 310 collimates an incoming light beam (from the tip lens side of exit lens 310) and deflects the incoming light beam to the focal point of exit lens 310. One of ordinary skill in the art will understand that increasing the focal length of exit lens 310 decreases the angle between the first beam 322 and second beam (340, 350 or 360). With a fixed focal length, a finite number of output angles between the two output beams can be chosen by selecting the output of optical switch 308. One of ordinary skill in the art will understand that smaller inter-fiber distances allow smaller output angles between beams exiting exit lens 310.

FIG. 4 is a block diagram showing a multi-beam configuration unit in accordance with another embodiment. More particularly, FIG. 4 illustrates an MBCU 400 that includes a frame 402, exit lens 411, and optical fibers with tip lenses. In an alternate embodiment, frame 402 can be omitted. In an alternate embodiment, one or more components of MBCU 400 can be configured outside frame 402. One of ordinary skill in the art will understand that other configurations can also be employed. In the illustrated embodiment, an input port 404 directs incoming light through an otherwise conventional single mode fiber 410, which is held in a fixed orientation and position by a plate 412. In the illustrated embodiment, plate 412 is an otherwise conventional V-groove plate. One of ordinary skill in the art will understand that other structures can also be employed.

In the illustrated embodiment, fiber 410 couples to a tip lens 414. In the illustrated embodiment, tip lens 414 is aligned to be coaxial with fiber 410. Light exiting fiber 410 through tip lens 414 forms a beam 416 that impinges upon exit lens 411, at or near the center of exit lens 411, which generates a collimated output beam 418.

In the illustrated embodiment, an input port 406 directs incoming light through an otherwise conventional single mode fiber 420, which is held in a fixed orientation parallel to fiber 410 by a plate 422. In the illustrated embodiment, plate 422 is an otherwise conventional V-groove plate. In the illustrated embodiment, fiber 420 couples to a tip lens 424. In the illustrated embodiment, tip lens 424 is aligned to be coaxial with fiber 420. Light exiting fiber 420 through tip lens 424 forms a beam 428 that impinges upon exit lens 411, at a location determined by the position of fiber 420, which generates a collimated output beam 430.

As described above, plate 422 holds fiber 420 in a fixed orientation parallel to fiber 410. However, in the illustrated embodiment, plate 422 is coupled to a micrometer translation stage 408 configured to translate fiber 420 through a plurality of positions relative to fiber 410. More particularly, in the illustrated embodiment, stage 408 translates fiber 420 (and tip lens 424) in a perpendicular direction $X_4$ to the axes of both fiber 422 and fiber 410.

So configured, beam 428 can be moved to impinge upon exit lens 411 at a plurality of locations. One of ordinary skill in the art will understand that this translation varies the angle between beams 418 and 430, while maintaining the same intersection point between the beams. Generally, the intersection point of beams 418 and 430 is configured to lie on a desired position of the scanning system to which MBCU 400 couples. One of ordinary skill in the art will understand that substituting a translation stage for an optical switch allows for changing the angle between beams 418 and 430 in a continuous manner.

FIG. 5 is a block diagram showing a multi-beam configuration unit in accordance with still another embodiment. In particular, FIG. 5 illustrates an MBCU 500 configured with an optical switch, a plurality of optical fibers and tip lenses, a first exit lens, and a second exit lens. In the illustrated embodiment, MBCU 500 includes a frame 502, configured to provide a structure to which one or more of the various components of MBCU 500 can be fixed in a static orientation and/or position in space. In an alternate embodiment, frame 502 can be omitted. In an alternate embodiment, one or more components of MBCU 500 can be configured outside frame 502. One of ordinary skill in the art will understand that other configurations can also be employed.

MBCU 500 includes input ports 504 and 506, which couple to frame 502. In the illustrated embodiment, input port 504 couples received light to an otherwise conventional single mode fiber 514. A plate 516 holds fiber 514 in a fixed orientation relative to exit lens 510. In the illustrated embodiment, plate 516 is an otherwise conventional V-groove plate. One of ordinary skill in the art will understand that other suitable mechanisms can be employed to hold fiber 514 in a fixed orientation.

In the illustrated embodiment, the surface tip of fiber 514 couples to a tip lens 518 in a co-axial alignment. In the illustrated embodiment, output beam 520 of tip lens 518 impinges upon exit lens 510 at or near the center of exit lens 510. In the illustrated embodiment, the resultant beam, beam 522, impinges upon exit lens 512 at or near the center of exit lens 512. In the illustrated embodiment, the resultant beam, output beam 524, is collimated.

In the illustrated embodiment, input port 506 is configured to couple received input light to an otherwise conventional optical switch 508. In the illustrated embodiment, optical switch 508 is configured to direct received light to one of three ports 528, 530, and 532. Generally, each of optical ports 528, 530, and 532 is configured to route received light along a path having a particular orientation in space relative to the path of optical fiber 514.

In the illustrated embodiment, ports 528, 530, and 532 are coupled to otherwise conventional single mode fibers 534, 546, and 556, respectively. Fibers 534, 546, and 556 are coupled to tip lenses 536, 548, and 558, respectively. In the illustrated embodiment, each of fibers 534, 546, and 556 (and their associated tip lenses) are held in a fixed orientation by plate 516, such that their directions intersect at a common point that corresponds to the focal point of exit lens 510.

So configured, optical switch 508 can be operated to direct incoming light along one of fibers 534, 546, and 556, thereby selecting one of beams 538, 550, and 560, respectively. In the illustrated embodiment, beam 538 has been selected. Each of beams 538, 550, and 560 impinge on exit lens 510, generating beams 540, 552, and 562, respectively. Each of beams 540, 552, and 562 impinge on exit lens 512, generating beams 544, 554, and 564, respectively. Generally, exit lens 512 collimates an incoming light beam (from the tip lens side of exit lens 512) and deflects the incoming light beam to the focal point of exit lens 512. One of ordinary skill in the art will understand that with a fixed focal length of exit lens 512, a finite number of output angles between the output beams 524 and one of 544, 554, and 564 can be chosen by selecting the output of optical switch 508.

FIG. 6 is a block diagram showing a multi-beam configuration unit in accordance with yet another embodiment. More particularly, FIG. 6 illustrates an MBCU 600 that includes a frame 602, first exit lens 610, second exit lens 612, and optical fibers with tip lenses. In an alternate embodiment, frame 602 can be omitted. In an alternate embodiment, one or more components of MBCU 600 can be configured outside frame 602. One of ordinary skill in the art will understand that other configurations can also be employed. In the illustrated embodiment, an input port 604 directs incoming light through an otherwise conventional single mode fiber 614, which is held in a fixed orientation and position by a plate 616. In the illustrated embodiment, plate 616 is an otherwise conventional V-groove plate.

In the illustrated embodiment, fiber 614 couples to a tip lens 618, in co-axial alignment. Light exiting fiber 614 through tip lens 618 forms a beam 620 that impinges upon exit lens 610, at or near the center of exit lens 610, which generates an output beam 622. Beam 622 impinges upon exit lens 612, at or near the center of exit lens 612, which generates a collimated output beam 624.

In the illustrated embodiment, an input port 606 directs incoming light through an otherwise conventional single mode fiber 626, which is held in a fixed orientation for each measurement at an angle θ to fiber 614 by a plate 628. One of ordinary skill in the art will appreciate that angle θ can be adjusted for different measurements. In the illustrated embodiment, plate 628 is an otherwise conventional V-groove plate. In the illustrated embodiment, fiber 626 couples to a tip lens 634. In the illustrated embodiment, tip lens 634 is aligned to be coaxial with fiber 626. Light exiting fiber 626 through tip lens 634 forms a beam 638 that impinges upon exit lens 610, at a location determined by the position of fiber 626, which generates an output beam 640. Beam 640 impinges upon exit lens 612, generating a collimated output beam 642.

As described above, plate 628 holds fiber 626 in a particular orientation with respect to fiber 614. However, in the illustrated embodiment, plate 628 is coupled to a micrometer translation stage 630 configured to translate plate 628 along a track 632 through a plurality of positions relative to fiber 614, as generally indicated by the arrow $X_6$. More particularly, in the illustrated embodiment, stage 630 translates fiber 626 (and tip lens 634) such that beam 638 always intersects beam 620 at the focal point of exit lens 610. In the illustrated embodiment, plate 628 also includes a plurality of tracks 608 that can be configured to receive additional plates 628 with additional fiber and tip lens pairs and that can be translated along track 632.

So configured, beam 638 can be moved to impinge upon exit lens 610 at a plurality of locations. One of ordinary skill in the art will understand that this translation varies the angle between beams 624 and 642, while maintaining the same intersection point between the beams. Generally, the intersection point of beams 624 and 642 is configured to lie on a desired position of the scanning system to which MBCU 600 couples. Additionally, exit lenses 610 and 612 can be configured to increase or decrease the diameter of beams 624 and 642. As described above with respect to FIG. 4, one of ordinary skill in the art will understand that substituting a translation stage for an optical switch allows for changing the angle between beams 624 and 642 in a continuous manner.

Figure 7:
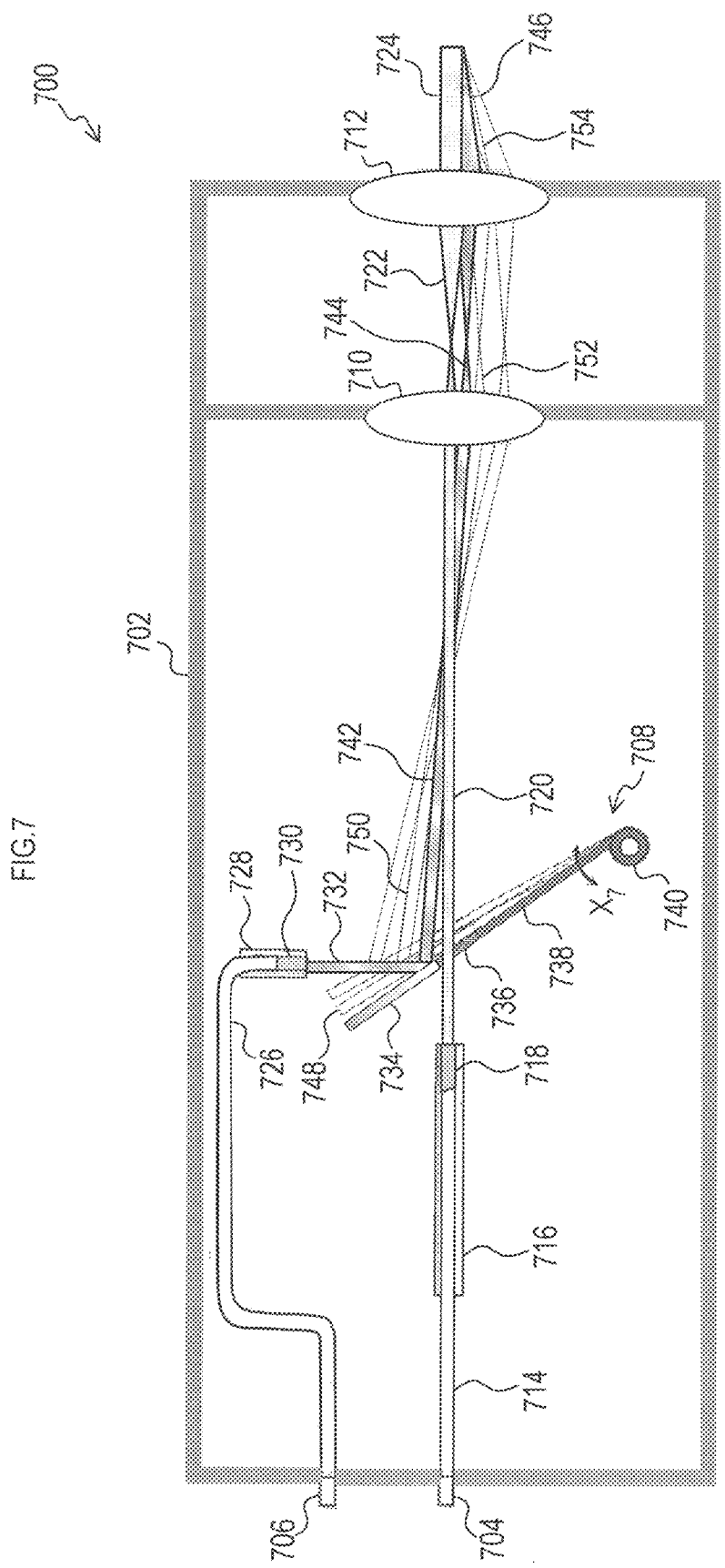
FIG. 7 is a block diagram showing a multi-beam configuration unit in accordance with still another embodiment.

FIG. 7 is a block diagram showing a multi-beam configuration unit in accordance with still another embodiment. More particularly, FIG. 7 illustrates an MBCU 700 that includes a frame 702, first exit lens 710, second exit lens 712, optical fibers with tip lenses, and a mirror assembly 708. In an alternate embodiment, frame 702 can be omitted. In an alternate embodiment, one or more components of MBCU 700 can be configured outside frame 702. One of ordinary skill in the art will understand that other configurations can also be employed. In the illustrated embodiment, an input port 704 directs incoming light through an otherwise conventional single mode fiber 714, which is held in a fixed orientation and position by a plate 716. In the illustrated embodiment, plate 716 is an otherwise conventional V-groove plate.

In the illustrated embodiment, fiber 714 couples to a tip lens 718, in co-axial alignment. Light exiting fiber 714 through tip lens 718 forms a beam 720 that passes through window 736. In the illustrated embodiment, window 736 is a transparent section of mirror assembly 708. In an alternate embodiment, window 736 is an aperture. One of ordinary skill in the art will understand that other suitable configurations to allow beam 720 to pass unimpeded can also be employed. Beam 720 impinges upon exit lens 710, at or near the center of exit lens 710, which generates an output beam 722. Beam 722 impinges upon exit lens 712, at or near the center of exit lens 712, which generates a collimated output beam 724.

In the illustrated embodiment, an input port 706 directs incoming light through an otherwise conventional single mode fiber 726, which is held in a fixed orientation by a plate 728. In the illustrated embodiment, plate 728 is an otherwise conventional V-groove plate. In the illustrated embodiment, fiber 726 couples to a tip lens 730. In the illustrated embodiment, tip lens 730 is aligned to be coaxial with fiber 726. Light exiting fiber 726 through tip lens 730 forms a beam 732 that impinges upon a mirror 734 of mirror assembly 708. In the illustrated embodiment mirror 734 is a mirror. One of ordinary skill in the art will understand that any suitable reflective surface can also be employed.

Beam 732 reflects from mirror 734 in one of a plurality of orientations, based on the position of mirror 734. In the illustrated embodiment, mirror 734 couples to a mount 738 configured to be rotated around an axis by a hinge 740, as generally indicated by the arrow $X_7$. Generally, mirror assembly 708 is configured to move mirror 734 so that beam 732 reflects off of mirror 734 to intersect beam 720 at the focal point of lens 710. In one embodiment, by restricting motion to angles of rotations less than or equal to 1 degree, a continuous change of the angle between beam 720 and the beam reflecting from mirror 734 can maintain the same intersection point.

In the illustrated embodiment, with mirror 734 arranged as shown, beam 732 reflects from mirror 734 as beam 742. Beam 742 impinges upon exit lens 710, generating a beam 744. Beam 744 impinges upon exit lens 712, generating a collimated output beam 746. With mirror 734 moved to position 748, beam 732 reflects from mirror 734 as beam 750. Beam 750 impinges upon exit lens 710, generating a beam 752. Beam 752 impinges upon exit lens 712, generating a collimated output beam 754.

Generally, the intersection point of beams 724 and 746 is configured to lie on a desired position of the scanning system to which MBCU 700 couples. Additionally, exit lenses 710 and 712 can be configured to increase the diameter of beams 724 and 746. As described above with respect to FIG. 4, one of ordinary skill in the art will understand that substituting a translation stage for an optical switch allows for changing the angle between beams 724 and 746 in a continuous manner.

Figure 8:
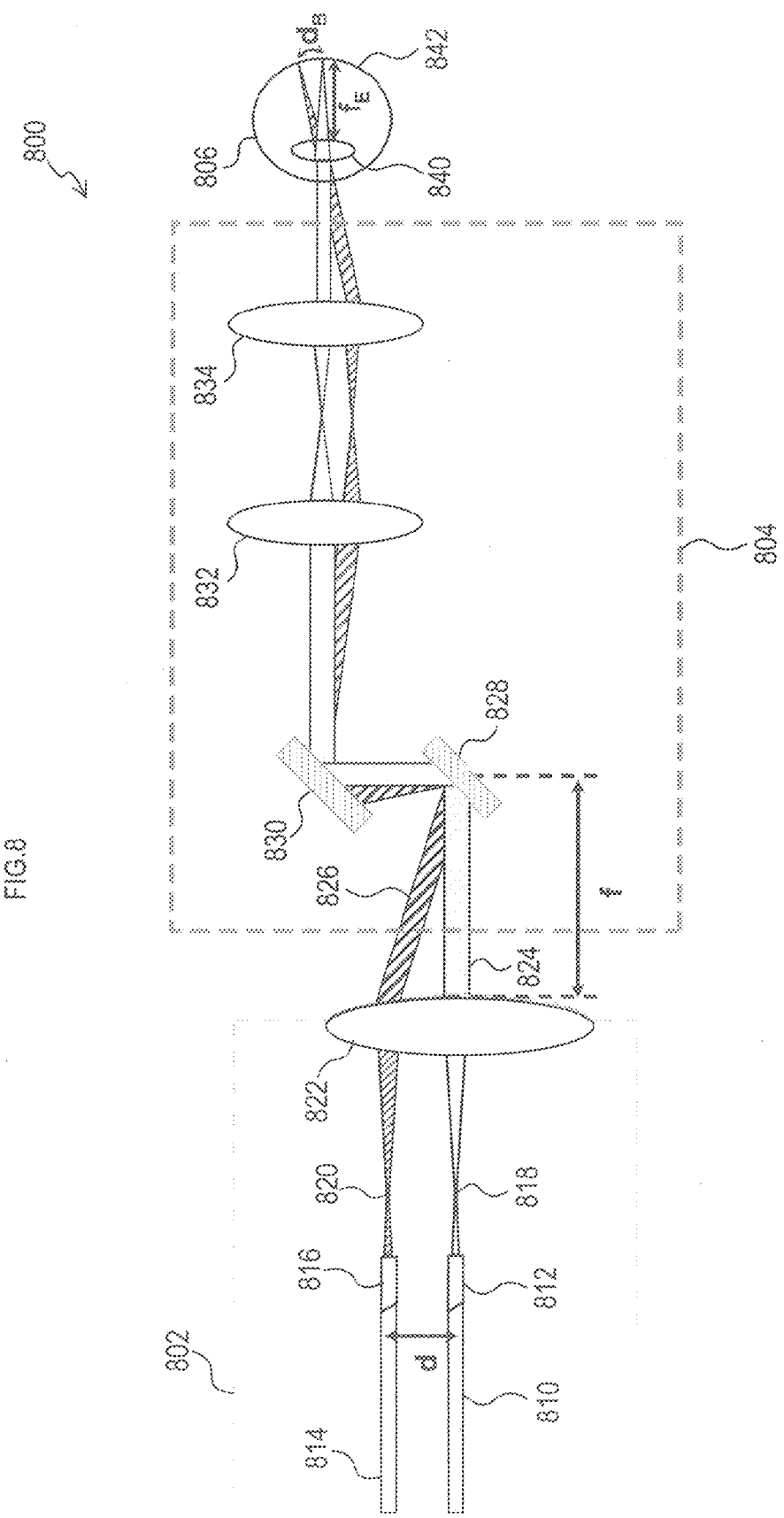
FIG. 8 is a block diagram showing a scan system in accordance with one embodiment.

FIG. 8 is a block diagram showing a scan system in accordance with one embodiment. Generally, FIG. 8 illustrates a system 800 showing the propagation of two scanning beams 824, 826 from an MBCU 802, through a scan system 804, to the retina 842 of an eye 806 in the case of spatially separated beams on the sample.

In the illustrated embodiment, MBCU 802 includes fibers 810 and 814, which are arranged in parallel and separated by a distance, d. Fibers 810 and 814 couple to tip lenses 812 and 816, respectively. Beams 818 and 820 leave tip lenses 812 and 816, impinging on exit lens 822 as collimated beams 824 and 826, respectively.

Beams 824 and 826 enter scan system 804, intersecting at the focal length, f, of exit lens 822. As shown, the focal point of exit lens 822 is configured to intersect at a scan mirror 828. Beams 824 and 826 reflect from scan mirror 828 to scan mirror 830, and then pass through lenses 832 and 834, before entering retina 840. As shown, beams 824 and 826 impinge on the sample, eye 806, at the scan surface 842 (in this case, the retina).

One of ordinary skill in the art will appreciate that there are well-known mathematical descriptions of the optical features shown. For example, the distance between beams 824 and 826 on the retina 842 is dB. In this configuration, the beam distance dB as a function of the inter-fiber distance d can be computed.

For the following discussion, the following definitions apply:
d=distance between lenses 812 and 816, or fiber inter-distance between fibers 810 and 814
f=focal length of lens 822
a=angular magnification due to optics between exit lens 822 and retina 842
fE=distance between the pupil and retina 842
dB=distance between beams 824 and 826 on retina 842
SR=the scanning range of the B-scan on the retina 842
NA=the number of A-lines per B-scan
fA=the A-line acquisition rate
Δt=the time interval between beams 824 and 826 along the scanning direction It can be written:

$$dB = fE \text{ TAN} [aA \text{ TAN}(d/f)]$$

Moreover:

$dB = f A \Delta t SR/NA.$

Therefore:

$d = f \text{TAN} \{A \text{ TAN} [f A \Delta t SR/(NA fE)]/a\}.$

For clarity of explanation, a specific, non-limiting, numerical example for spatially separated scanning beams will be provided. In one embodiment, based on plausible measurement system and sample parameters, examples of numerical values for inter-fiber distances that allow the measurement of blood axial velocities in human eye are now given. For example, to be sensitive to retinal capillaries having fast blood velocities, the time interval Δt is of the order of 0.18 ms between scanning beams on the retina. Assuming: f=150 mm, a=3, fE=17 mm, SR=6 mm, NA=1000 and fA=100 kHz, an inter-fiber distance of d=318 micrometers is obtained. Consequently, the inter-fiber distance, in one embodiment, must be on the order of the optical fiber diameter. Further, to be sensitive to slower blood velocities or vessels that are oriented at angles close to 90 degrees with respect to the scanning beams, a larger time interval, Δt of the order of 5 ms, is required. This gives an inter-fiber distance of 8.7 mm, in one embodiment. One of ordinary skill in the art will understand that these values are provided as exemplary only.

Figure 9:
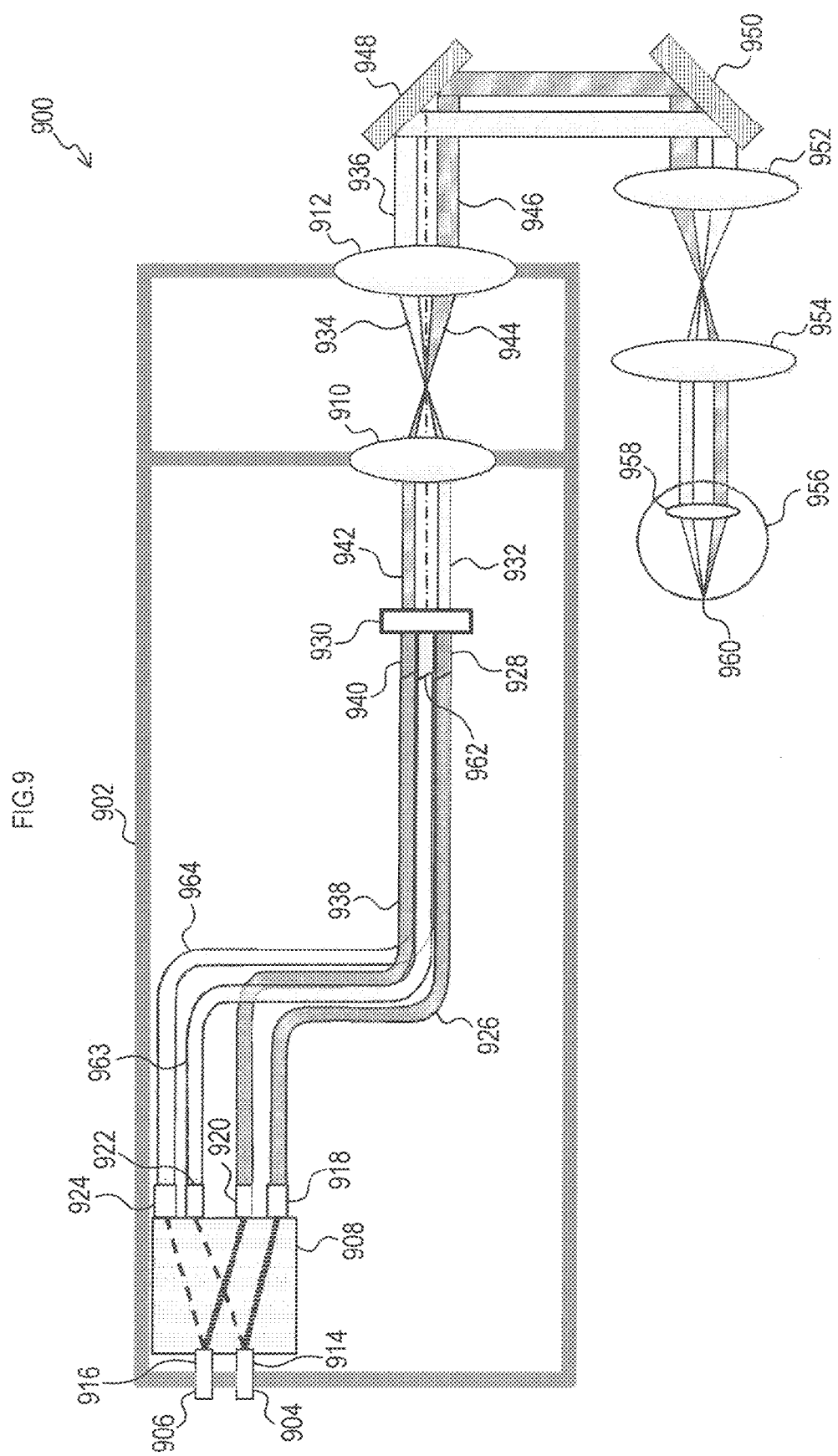
FIG. 9 is a block diagram showing a multi-beam configuration unit and a scan system in accordance with one embodiment.

As described above, the disclosed embodiments can be configured for either spatially or angularly separated beams. FIG. 9 is a block diagram showing a multi-beam configuration unit and a scan system in accordance with one embodiment. In particular, FIG. 9 illustrates an MBCU and scan system 900 configured to provide two collimated parallel beams that will impinge onto the sample at two different incident angles.

In the illustrated embodiment, system 900 includes a frame 902 configured to fix the various components in a particular orientation in space. In an alternate embodiment, frame 902 can be omitted. In an alternate embodiment, one or more components of MBCU 900 can be configured outside frame 902. One of ordinary skill in the art will understand that other configurations can also be employed. Input ports 904 and 906 are configured to receive non-polarized source input and to direct received input to (and from) optical switch 908. In the illustrated embodiment, input port 904 couples to switch selector 914, which directs light from input port 904 to one of outputs 918 and 922. Similarly, input port 906 couples to switch selector 916, which directs light from input port 906 to one of outputs 920 and 924. Outputs 918, 920, 922, and 924 couple to otherwise conventional single mode fibers 926, 938, 963, and 964, respectively.

Each of fiber 926, 938, 963, and 964 couple to a corresponding tip lens 928, 940, 962, and 1002 (of FIG. 10), respectively. Each of fiber 926, 938, 963, and 964 couples to a mount 930. In the illustrated embodiment, each of fiber 926, 938, 963, and 964 couples to mount 930 through a respective tip lens.

In operation, optical switch 908 is configured to select between two pairs of parallel aligned fibers, either fibers 926 and 938, or fibers 963 and 964. In the illustrated embodiment, fibers 926 and 938 are shown as the selected pair of fibers. Thus, light from input ports 904 and 906 leave tip lenses 928 and 940 as collimated beams 932 and 942, respectively.

Beams 932 and 942 impinge upon exit lens 910, generating beams 934 and 944, respectively. Beams 934 and 944 impinge upon exit lens 912, generating collimated beams 936 and 946, respectively. In the illustrated embodiment, beams 936 and 946 enter the scan system, reflecting from mirror 948 to mirror 950, and from mirror 950 through lenses 952 and 954 to sample 956. Beams 936 and 946 enter sample 956 through lens 958, impinging upon sample 956 at a point 960. As shown, beams 936 and 946 arrive at point 960 at different incident angles, as described in more detail below.

As described above, in system 900, beams are paired into parallel pairs of beams, the selected pair being engaged by the optical switch 908. In the illustrated embodiment, the orientation of the pairs is fixed in two perpendicular planes. One of ordinary skill in the art will understand that other configurations can also be employed. For example, in an alternate embodiment, system 900 includes two additional fiber pairs, the added pairs lying in planes perpendicular to each other and at a 45 degree angle from the planes defined by the pair of fibers 926 and 938.

FIG. 10 is a block diagram showing an aspect of the multi-beam configuration unit of FIG. 9 in accordance with one embodiment. In particular, FIGS. 10A and 10B present a clearer view, in one embodiment, of the arrangement of the fiber pairs of FIG. 9, relative to each other. Generally, system 1000 includes fibers 926, 938, 963, and 964, shown co-axially coupled to their associated tip lenses, which are mounted in a fixed orientation and position on a mount 930.

As described above, light beams exit the tip lenses based on, among other things, the orientation in space of the tip lenses. FIG. 10B shows an end view of the tip lenses, in one embodiment. In the illustrated embodiment, tip lenses 928 and 940 represent a first pair, the "vertically aligned" pair. Similarly, tip lenses 962 and 1002 represent a second pair, the "horizontally aligned" pair.

As shown the first pair and the second pair are arranged perpendicular to each other. Additionally, the midpoint between the first pair of tip lenses and the midpoint of the second pair of tip lenses are aligned to be coincident on mount 930. As described above, an optical switch selects between the pairs, and in one embodiment, light beams exit from and return through only the selected pair of tip lenses. In one embodiment, light returning from the sample can return through all four tip lenses, however, as one skilled in the art will understand, the operation of the optical switch prevents light from passing through the non-selected lens pair beyond the optical switch. Moreover, as described in more detail below, in an alternate embodiment, sometimes referred to herein as a "passive" configuration, light is sent to the sample from a single tip lens (or lens pair) and is permitted to return from the sample for processing along all four tip lenses.

As described above with respect to FIG. 9, in the selected fiber pair, beam 936 exits from tip lens 928 as beam 932 and beam 946 exits from tip lens 940 as beam 942. If the optical switch is instead set to select the other fiber pair, beam 936 exits from tip lens 962 as beam 932 and beam 946 exits from tip lens 1002 as beam 942. As such, in the illustrated embodiment, beams 936 and 946 can be configured to impinge upon the same point on the sample, in two different planes depending on whether the "vertically aligned" or the "horizontally aligned" pair is selected. So configured, measurements conducted at the same sample point, from different alignments can be achieved.

Figure 12:
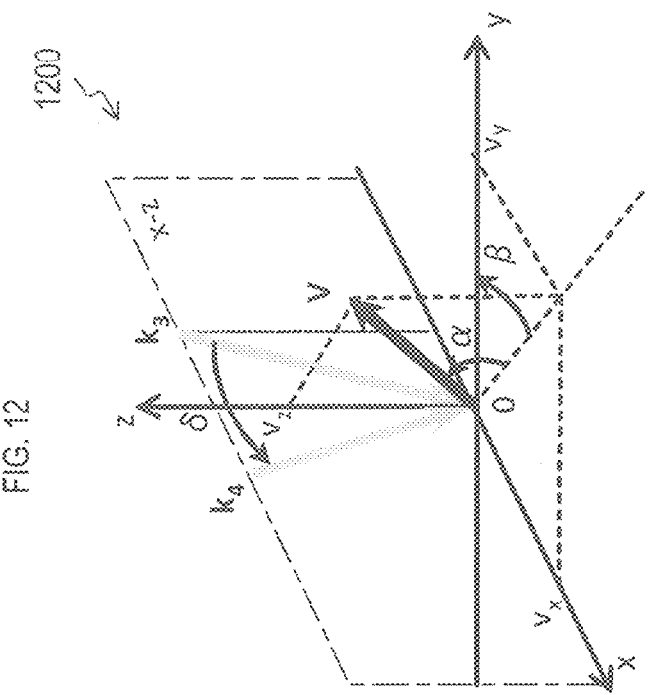
FIGS. 11-12 are vector diagrams showing operation of a multi-channel optical coherence tomography apparatus and method in accordance with one embodiment.
Figure 11:
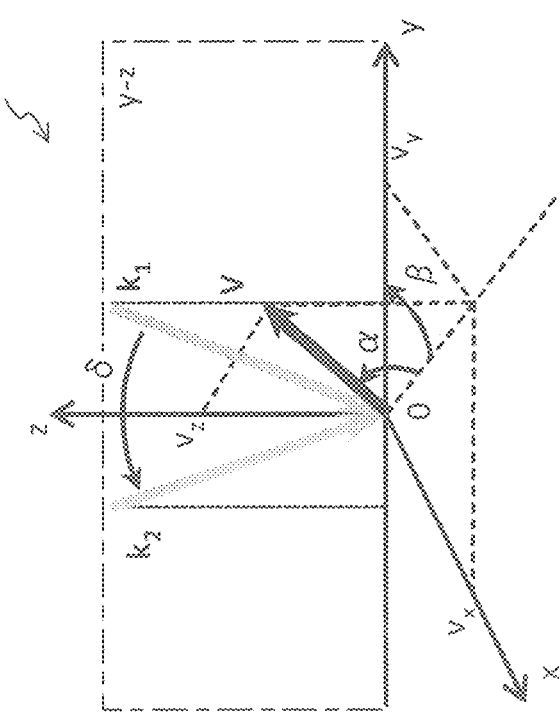

FIGS. 11-12 are vector diagrams showing operation of a multi-channel optical coherence tomography apparatus and method in accordance with one embodiment, in additional detail. FIG. 11 illustrates a coordinate system in graph 1100, in which example vectors representing scanning beams are depicted. In the illustrated embodiment, a sample velocity vector V and two incident bidirectional beams k1 and k2, lie in the y-z plane.

In the illustrated embodiment of FIG. 11, the vertically aligned pair of beams has been selected. The origin of the frame (x, y, z) corresponds to the measurement point on the sample eye. The z-axis represents the optical axis of the sample eye. The first scan beam (e.g., beam 936 of FIG. 9) is represented by the vector k1 and the second scan beam (e.g., beam 946 of FIG. 9) is represented by vector k2. As shown, vectors k1 and k2 lie in the plane y-z and are symmetric with respect to z-axis. The angle between k1 and k2 is δ. The vector V=(Vx, Vy, Vz) represents the velocity vector of a scattering point inside the sample located at the origin of the frame (x, y, z). One of ordinary skill in the art will understand that V represents the motion information desired by the OCT process, in one embodiment.

The vector V with respect to the z-axis makes an angle (π/2−α). The projection vector of V onto the plane x-y makes an angle β with the y-axis. As the sample is scanned laterally, for each beam the phase difference between two A-lines (or B-scans) can be computed, as in conventional Doppler. For the following discussion, Δϕ1 and Δϕ2 refer to the phase differences between A-lines (or B-scans) for vectors (beams) k1 and k2, respectively:

$$\Delta\phi1 = 2Tk1 \cdot V = 2TkV[\sin(\delta/2)\cos(\alpha)\cos(\beta) - \cos(\delta/2)\sin(\alpha)] \quad (1)$$

$$\Delta\phi2 = 2Tk2 \cdot V = 2TkV[-\sin(\delta/2)\cos(\alpha)\cos(\beta) - \cos(\delta/2)\sin(\alpha)] \quad (2)$$

where T is, for example, the time between two A-lines or B-scans, k=2πn/λ, n is the refractive index of the sample, λ is the wavelength of the light source, and V the absolute velocity of sample at this location. δ can be approximated from the eye's optical power, if known or estimated.

It can be then written:

$$\Delta\phi a = \Delta\phi1 - \Delta\phi2 = 4TkV\sin(\delta/2)\cos(\alpha)\cos(\beta) \quad (3)$$

$$\Delta\phi1 + \Delta\phi2 = -4TkV\cos(\delta/2)\sin(\alpha) \quad (4)$$

Which will become useful in conjunction with the measurements obtained from the horizontally aligned beams.

FIG. 12 illustrates a coordinate system in graph 1200, in which example vectors representing scanning beams are depicted. In the illustrated embodiment, a sample velocity vector V and two incident bidirectional beams, k3 and k4, lie in the x-z plane.

In the illustrated embodiment of FIG. 12, the horizontally aligned pair of beams has been selected. The origin of the frame (x, y, z) corresponds to the measurement point on the sample eye. The z-axis represents the optical axis of the sample eye. The first scan beam (e.g., beam 936 of FIG. 9) is represented by the vector k3 and the second scan beam (e.g., beam 946 of FIG. 9) is represented by vector k4. As shown, vectors k3 and k4 lie in the plane x-z and are symmetric with respect to z-axis. The angle between k3 and k4 is 5.

The vector V with respect to the z-axis makes an angle (π/2−α). The projection vector of V onto the plane x-y makes an angle β with the y-axis. By replacing k1 and k2 by k3 and k4 respectively in the previous calculus:

$$\Delta\phi b = \Delta\phi3 - \Delta\phi4 = 4TkV\sin(\delta/2)\cos(\alpha)\sin(\beta) \quad (5)$$

To solve for V, two unknowns α and β need to be determined. In order to determine β, equations (3) and (5), for example, give:

$$\Delta\phi b/\Delta\phi a = \tan(\beta)$$

Which can be rewritten as:

$$\beta = a\tan(\Delta\phi b/\Delta\phi a) \quad (6)$$

Once β is known, α is obtained from equations (3) and (4):

$$(\Delta\phi1+\Delta\phi2)/(\Delta\phi1-\Delta\phi2) = -\tan(\alpha)/\tan(\delta/2)/\cos(\beta)$$

Which can be rewritten as:

$$\alpha = a\tan[-\tan(\delta/2)\cos(\beta)(\Delta\phi1+\Delta\phi2)/(\Delta\phi1-\Delta\phi2)] \quad (7)$$

Once β and α are known, the absolute velocity V from above expressions is obtained. Using equation (3) for example if β is far from π/2:

$$V = (\Delta\phi1 - \Delta\phi2)/[4Tk\sin(\delta/2)\cos(\alpha)\cos(\beta)]$$

or equation (5) for example if β is far from 0:

$$V = (\Delta\phi3 - \Delta\phi4)/[4Tk\sin(\delta/2)\cos(\alpha)\sin(\beta)]$$

One having ordinary skill in the art will understand that an ideal measurement would acquire these four signals simultaneously. As such, one having ordinary skill in the art will understand how to modify the system shown in FIG. 9, for example, to eliminate optical switch 908. Further, as the embodiment of FIG. 9 shows only two simultaneous scanning beams, one of ordinary skill in the art will understand that measurement of the sample to obtain motion information require successive use of the vertically aligned beams and the horizontally aligned beams. One of ordinary skill in the art will also appreciate that successive measurement entails the assumption that the velocity does not significantly change between the configuration change.

Figure 13:
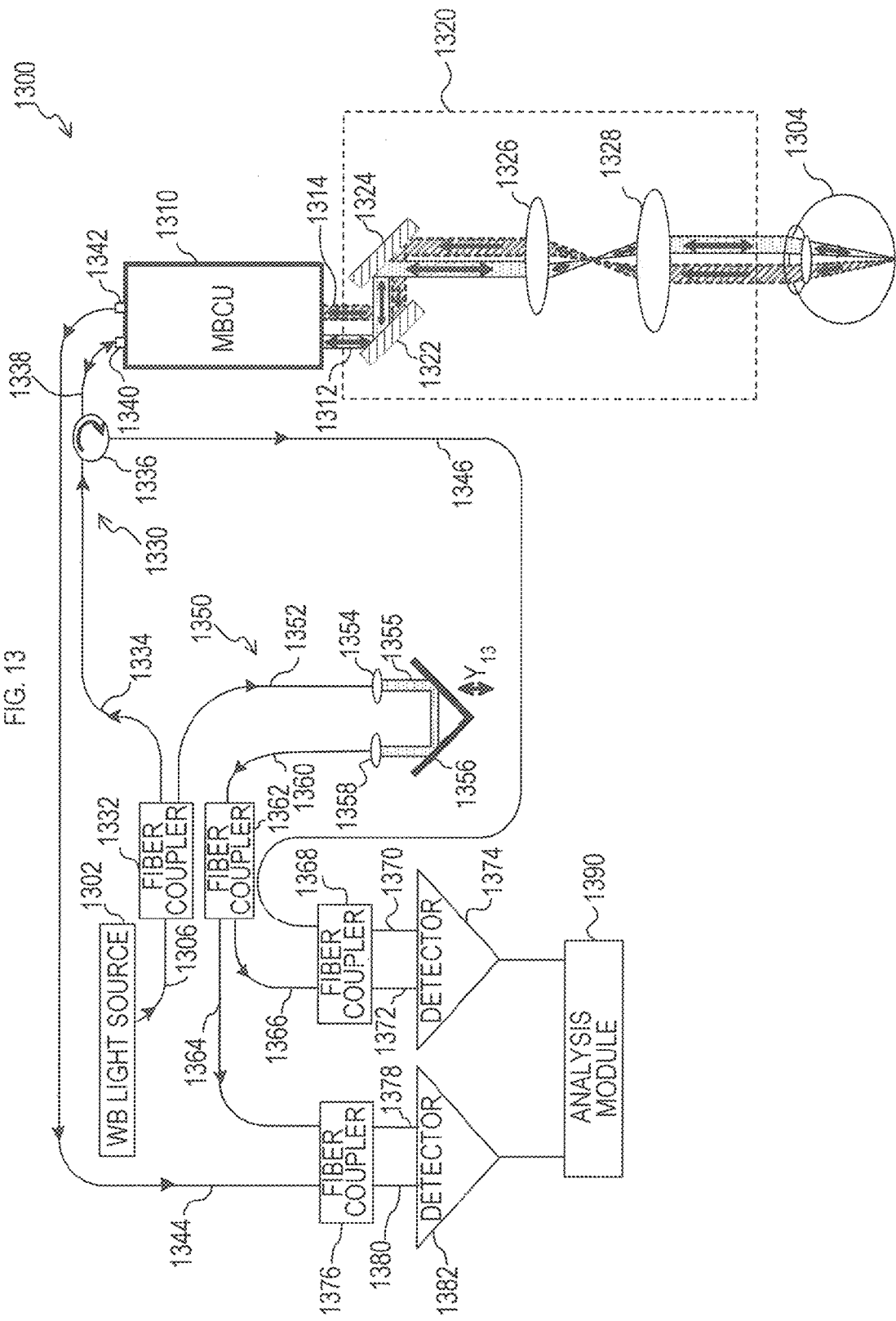
FIG. 13 is a block diagram showing a multi-channel optical coherence tomography apparatus in accordance with another embodiment.

Generally, the disclosed embodiments are mostly described with respect to embodiments employing the same number of active beams as the number of beams returning along paths from the sample. FIG. 13 shows an embodiment that can be configured with one active beam, collecting light from multiple return paths. FIG. 13 is a block diagram showing a multi-channel optical coherence tomography apparatus in accordance with one embodiment.

Specifically, FIG. 13 shows a multi-channel OCT system 1300 that includes a wideband (WB) light source 1302, a multi-beam configuration unit (MBCU) 1310, a scan system 1320, a sample arm 1330, and a reference arm 1350. One of ordinary skill in the art will understand that system 1300 operates on similar principles as those of system 100 of FIG. 1 and system 200 of FIG. 2, as modified as described below.

For example, generally, WB light source 1302 is an otherwise conventional light source that generates wideband source light, which is coupled to otherwise conventional single mode fiber 1306. Fiber 1306 delivers light from source 1302 to an otherwise conventional 1×2 fiber coupler 1332. Light entering fiber coupler 1332 from fiber 1306 passes to sample arm 1330, through an otherwise conventional single mode fiber 1334, and to reference arm 1350, through an otherwise conventional single mode fiber 1352.

In the illustrated embodiment, light passing from fiber coupler 1332 along fiber 1334 enters a bi-directional transmitter 1336. In the illustrated embodiment, bi-directional transmitter 1336 is an otherwise conventional optical circulator. In an alternate embodiment, other suitable equivalents can also be employed. One of ordinary skill in the art will understand that in the illustrated configuration, light from single mode fiber 1334 passes through transmitter 1336 into otherwise conventional single mode fiber 1338, and then into MBCU 1310 at an entry port 1340.

As described in more detail below, light entering MBCU 1310 at port 1340 is configured by MBCU 1310 to generate an active beam 1312. In the illustrated embodiment, only beams 1312 enters scan system 1320 from MBCU 1310, which manipulates the received beam according to a selected scanning protocol to scan sample 1304. In the illustrated embodiment, scan system 1320 includes a scanning mirror 1322, a scanning mirror 1324, a lens 1326, and a lens 1328.

Beam 1312 leaves scan system 1320 and impinges upon sample 1304, generating light that reflects back through scan system 1320 and MBCU 1310 along the paths taken by beams 1312 and 1314. In the illustrated embodiment, light from beam 1312 reflected by sample 1304 couples from MBCU 1310 at port 1340 into fiber 1338. However, in the illustrated embodiment, light from beam 1312 is also reflected by sample 1304 (along the path of beam 1314) and couples from MBCU 1310 at port 1342 into fiber 1344.

In the illustrated embodiment, light returning from sample 1304 along fiber 1344 is directed to a fiber coupler 1376. Light returning from sample 1304 along fiber 1338 is redirected by transmitter 1336 and otherwise conventional single mode fiber 1346 to an otherwise conventional 2×2 fiber coupler 1368.

As described above, fiber coupler 1332 also couples light from source 1302 to reference arm 1350. In the illustrated embodiment, fiber coupler 1332 couples light from source 1302 to an otherwise conventional single mode fiber 1352. Fiber 1352 couples received light to an otherwise conventional collimator lens 1354, which generates a reference beam 1355, which leaves lens 1354 to impinge upon a mirror 1356 (adjustable along the direction indicated by arrow $Y_{13}$), reflecting light into an otherwise conventional condensing lens 1358. Condensing lens 1358 couples the reference light from beam 1355 to an otherwise conventional single-mode fiber 1360, which delivers the light as a reference beam to otherwise conventional 1×2 fiber coupler 1362. Fiber coupler 1362 delivers the reference beam to otherwise conventional fibers 1364 and 1366.

Fiber coupler 1376 couples the light from fiber 1344 and the reference beam in fiber 1364 to generate a first interference signal, which fiber coupler 1376 delivers to an otherwise conventional detector 1382, via fibers 1378 and 1380. Similarly, fiber coupler 1368 couples the light from fiber 1346 and the reference beam in fiber 1366 to generate a second interference signal, which fiber coupler 1368 delivers to an otherwise conventional detector 1374, via fibers 1370 and 1372.

In the illustrated embodiment, detector 1382 generates a first scan signal based on the received first interference signal and delivers the first scan signal to analysis module 1390. Similarly, detector 1374 generates a second scan signal based on the received second interference signal and delivers the second scan signal to analysis module 1390. Generally, analysis module 1390 is configured to filter, amplify, digitize, and otherwise process the first and second scan signals to obtain volumetric, structural, and/or motion information about sample 1304, as described in more detail below.

As described above, in one configuration MBCU 1310 is configured to select between the vertically aligned fiber pair and the horizontally aligned fiber pair. Additionally, in the illustrated embodiment, system 1300 is configured with a single scanning beam and two return paths. Thus, one of ordinary skill in the art will appreciate that the previously discussed parameters T, k1, k2, k3, V, δ, α, and β are as described with respect to FIGS. 11 and 12, except that system 1300 uses vectors k2 in collection mode only, and does not use vector k4. As such, when light is illuminating the sample in the direction k1 and collecting light in direction −k1, the phase difference between two returning beams can be written as:

$$\Delta\phi 1 = 2Tk1 \cdot V = 2TkV[\sin(\delta/2)\cos(\alpha)\cos(\beta) - \cos(\delta/2)\sin(\alpha)] \quad (8)$$

When light is illuminating the sample in the direction k1 and collecting light in direction −k2, the phase difference between two instants is:

$$\Delta\phi 12 = T(k1+k2) \cdot V = -2TkV[\cos(\delta/2)\sin(\alpha)]. \quad (9)$$

When light is illuminating the sample in the direction k3 and collecting light in direction −k3, the phase difference between two instants can be written as:

$$\Delta\phi 3 = 2Tk3 \cdot V = 2TkV[\sin(\delta/2)\cos(\alpha)\sin(\beta) - \cos(\delta/2)\sin(\alpha)] \quad (10)$$

When light is illuminating the sample in the direction k3 and collecting light in direction −k2, the phase difference between two instants is given by:

$$\Delta\phi 32 = T(k3+k2) \cdot V = TkV[\sin(\delta/2)\cos(\alpha)\{\sin(\beta) - \cos(\beta)\} - 2\cos(\delta/2)\sin(\alpha)] \quad (11)$$

Angle β is obtained by using (8), (9), and (10), such as:

$$(\Delta\phi 3 - \Delta\phi 12)/(\Delta\phi 1 - \Delta\phi 12) = \tan(\beta) \quad (12)$$

Once β is known, and assuming δ known, α can be retrieved using:

$$(\Delta\phi 32 - \Delta\phi 12)/\Delta\phi 12 = -0.5\tan(\delta/2)[\sin(\beta) - \cos(\beta)]/\tan(\alpha)$$

or $$\tan(\alpha) = -0.5\tan(\delta/2)[\sin(\beta) - \cos(\beta)]\Delta\phi 12/(\Delta\phi 32 - \Delta\phi 12) \quad (13)$$

Finally, once β and α are determined, the absolute velocity V can be obtained with any of the previous equations (8) to (11). Thus, in the illustrated embodiment, a first single illumination beam (direction k1) is used with two collection beams (−k1, −k2), followed by a second single illumination beam (direction k3) is used with two collection beams (−k3, −k2). One having ordinary skill in the art will also understand that a similar principle obtains to use simultaneously two illumination beams (k1, k3) and three collection pathways (−k1, −k2, −k3), or other suitable combinations. One having ordinary skill in the art will understand that appropriate modification may require alternative different detections schemes, path-length multiplexing, or other such techniques.

The previous embodiments considered embodiments having a separate detection arm and sample arm. The classic example of separate detection and sampling is shown by the Michelson interferometer. In contrast, the classic example of overlapping (wholly or partially) detection and sampling is shown by the Fizeau interferometer. The embodiments disclosed in FIGS. 14-17 show embodiments with overlapping or partially overlapping detection and sampling, and are sometimes referred to herein as "common path" embodiments.

FIG. 14 is a block diagram showing a multi-channel optical coherence tomography apparatus in accordance with still another embodiment. In particular, FIG. 14 shows a system 1400 configured with a WB light source 1402, an MBCU 1410, a scan system 1404, configured to scan a sample 1406.

Generally, source 1402 generates source light that is directed through fiber 1403 to bi-directional transmitter 1405, and then to fiber coupler 1414. Fiber coupler 1414 directs light through fibers 1416 and 1418, which are configured with different path lengths. Light passes from fiber 1416 to port 1420, though MBCU 1410, entering scan system 1404 as beam 1450. Light passes from fiber 1418 to port 1422, through MBCU 1410, entering the scan system 1404 as beam 1452.

In the illustrated embodiment, scan system 1404 includes an otherwise conventional partial reflector 1430. Beams 1450 and 1452 reflect from mirror 1424 to mirror 1426, through lens 1428, partially reflecting off of partial reflector 1430. One having ordinary skill in the art will understand that partial reflector 1430 thus generates reference signals that can be used to generate interference signals with the light returning from the sample 1406.

In the illustrated embodiment, the light reflecting from the sample and from the partial reflector 1430 return back through the optical paths to fiber coupler 1414 and transmitter 1405. The recombined light passes along fiber 1442 to a detection module 1440. Generally, detection module 1440 is configured to detect and analyze interference signals based on the combined light returning from the sample and the reference light, to perform OCT motion analysis.

In the illustrated embodiment, detection module 1440 is shown as a single abstract component. In an alternate embodiment, detection module 1440 includes a detector and analysis module. On having ordinary skill in the art will appreciate that other configurations can also be employed, including components configured for amplification, filtering, and other suitable techniques.

FIG. 15 is a block diagram showing a multi-channel optical coherence tomography apparatus in accordance with yet another embodiment. In particular, FIG. 15 shows a system 1500 configured with a WB light source 1502, an MBCU 1510, a scan system 1530, configured to scan a sample 1506.

Generally, source 1502 generates source light that is directed through fiber 1504 to fiber coupler 1520. Fiber coupler 1520 directs light through fibers 1560 and 1562 to bi-directional transmitters 1522 and 1524, respectively. Light passes from transmitters 1522 and 1524, through fibers 1564 and 1566, respectively. In the illustrated embodiment, fibers 1560 and 1562 are configured with different optical path lengths. Light from fibers 1564 and 1566 is directed to ports 1528 and 1526, respectively, and through MBCU 1510, entering scan system 1530 as beams 1552 and 1550, respectively.

In the illustrated embodiment, scan system 1530 includes an otherwise conventional partial reflector 1538. Beams 1550 and 1552 reflect from mirror 1532 to mirror 1534, through lens 1536, partially reflecting off of partial reflector 1538. One having ordinary skill in the art will understand that partial reflector 1538 thus generates reference signals that can be used to generate interference signals with the light returning from the sample 1506.

In the illustrated embodiment, the light reflecting from the sample and from the partial reflector 1538 return back through the optical paths to transmitters 1522 and 1524. Returning light passes from transmitter 1522 along fiber 1570 to a detection module 1576. Returning light passes from transmitter 1524 along fiber 1572 to a detection module 1574. Generally, detection modules 1574 and 1576 are configured to detect and analyze interference signals based on the combined light returning from the sample and the reference light, to perform OCT motion analysis.

Figure 16:
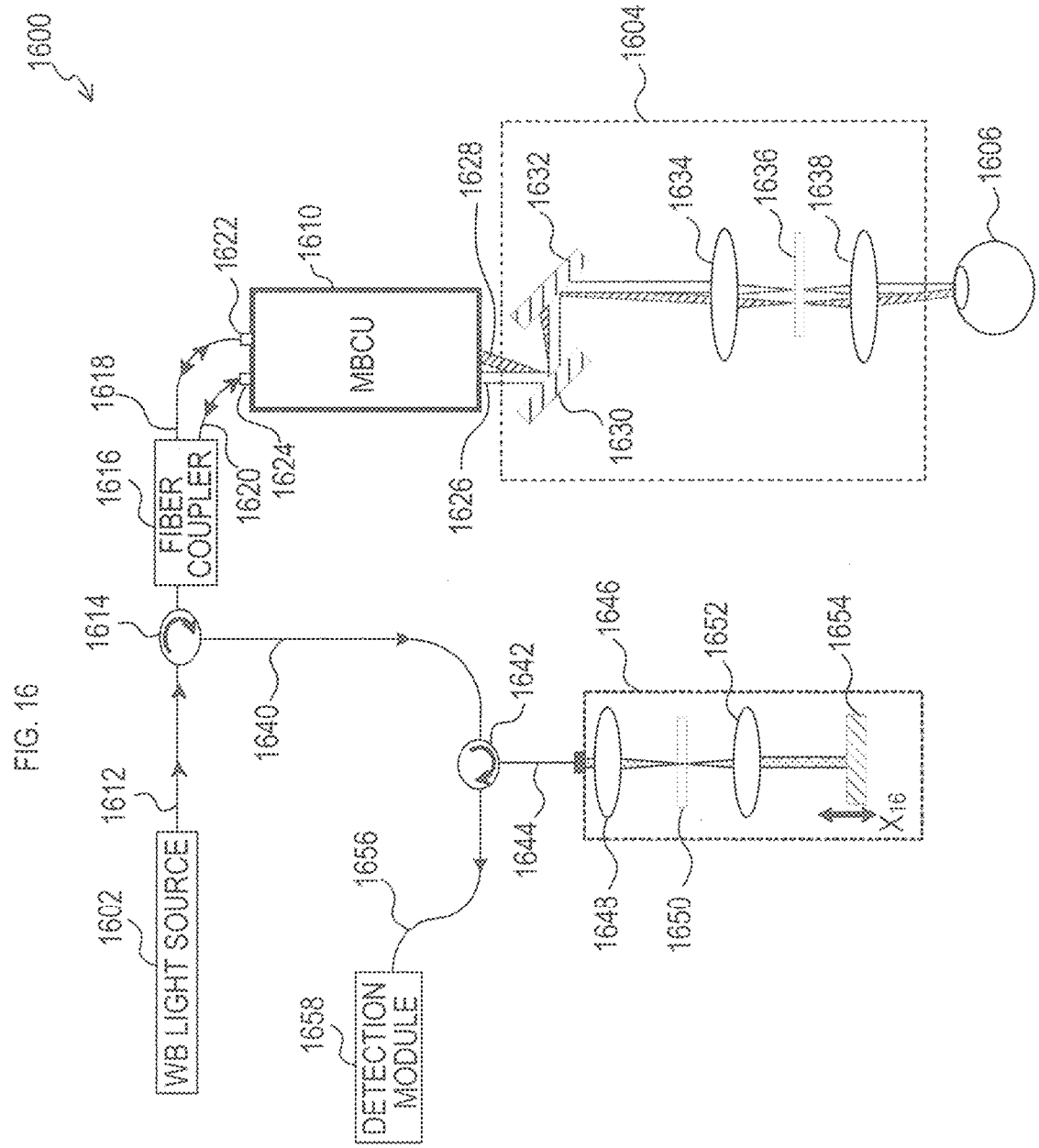
FIG. 16 is a block diagram showing a multi-channel optical coherence tomography apparatus in accordance with still another embodiment.

FIG. 16 is a block diagram showing a multi-channel optical coherence tomography apparatus in accordance with still another embodiment, generally an embodiment wherein the sample is not amenable to near access. In particular, FIG. 16 shows a system 1600 configured with a WB light source 1602, an MBCU 1610, a scan system 1604, configured to scan a sample 1606.

Generally, source 1602 generates source light that is directed through fiber 1612 to bi-directional transmitter 1614, and then to fiber coupler 1616. Fiber coupler 1616 directs light through fibers 1618 and 1620, which are configured with different path lengths. Light passes from fiber 1618 to port 1622, through MBCU 1610, entering scan system 1604 as beam 1628. Light passes from fiber 1620 to port 1624, through MBCU 1610, entering scan system 1604 as beam 1626.

In the illustrated embodiment, scan system 1604 includes an otherwise conventional partial reflector 1636, positioned between lenses 1634 and 1638. Beams 1626 and 1628 reflect from mirror 1630 to mirror 1632, through lens 1634, partially reflecting off of partial reflector 1636, before continuing through lens 1638 and on to sample 1606. One having ordinary skill in the art will understand that partial reflector 1636 thus generates reference signals that can be used to generate interference signals with the light returning from the sample 1606.

In the illustrated embodiment, the light reflecting from the sample and from the partial reflector 1636 return back through the optical paths to fiber coupler 1616 and transmitter 1614. The recombined light passes along fiber 1640 to a bi-directional transmitter 1642. The recombined light is thereby directed into a reference module 1646.

As shown in the illustrated embodiment, reference module 1646 is configured to generate an additional reference signal. In one embodiment, reference module 1646 is configured to match the path lengths between the reference and the sample signals. Generally, as one skilled in the art will understand, light enters module 1646, passes through lens 1648 and is partially reflected by partial reflector 1650. The light not reflected by partial reflector 1650 passes through lens 1652 before impinging upon mirror 1654, which is set with a configurable distance $X_{16}$.

Light returning from module 1646 passes along fibers 1644 and 1656 to detection module 1658. Generally, detection module 1658 is configured to detect and analyze interference signals based on the combined light returning from the sample and the reference light, to perform OCT motion analysis.

Figure 17:
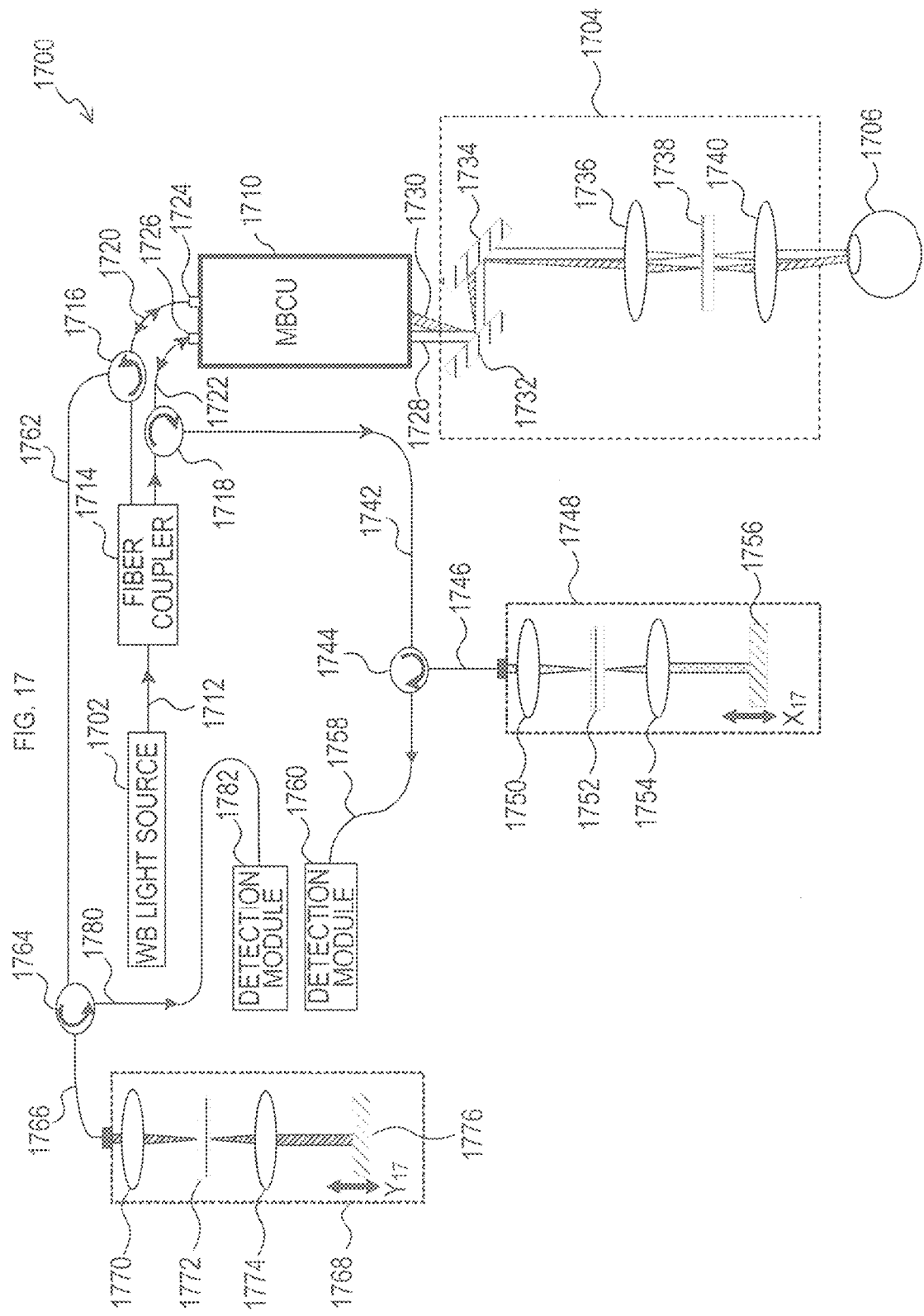
FIG. 17 is a block diagram showing a multi-channel optical coherence tomography apparatus in accordance with yet another embodiment.

FIG. 17 is a block diagram showing a multi-channel optical coherence tomography apparatus in accordance with yet another embodiment. In particular, FIG. 17 shows a system 1700 configured with a WB light source 1702, an MBCU 1710, a scan system 1704, configured to scan a sample 1706.

Generally, source 1702 generates source light that is directed through fiber 1712 to fiber coupler 1714. Fiber coupler 1714 directs light to bi-directional transmitters 1716 and 1718. Light passes from transmitters 1716 and 1718, through fibers 1720 and 1722, respectively. In the illustrated embodiment, fibers 1720 and 1722 are configured with different optical path lengths. Light from fibers 1720 and 1722 is directed to ports 1724 and 1726, respectively, and though MBCU 1710, entering scan system 1704 as beams 1730 and 1728, respectively.

In the illustrated embodiment, scan system 1704 includes an otherwise conventional partial reflector 1738. Beams 1728 and 1730 reflect from mirror 1732 to mirror 1734, through lens 1736, partially reflecting off of partial reflector 1738. One having ordinary skill in the art will understand that partial reflector 1738 thus generates reference signals that can be used to generate interference signals with the light returning from the sample 1706. Light not reflected by partial reflector 1738 passes through lens 1740, to impinge upon and reflect from, sample 1706.

In the illustrated embodiment, the light reflecting from the sample and from the partial reflector 1738 return back through the optical paths to transmitters 1716 and 1718. The recombined light passes from transmitter 1718 along fiber 1742 to a bi-directional transmitter 1744. The recombined light is thereby directed into a reference module 1748. As shown in the illustrated embodiment, light enters module 1748, passes through lens 1750 and is partially reflected by partial reflector 1752. The light not reflected by partial reflector 1752 passes through lens 1754 before impinging upon mirror 1756, which is set with a configurable distance $X_{17}$. Light returning from module 1748 passes along fibers 1746 and 1758 to detection module 1760.

The recombined light passes from transmitter 1716 along fiber 1762 to a bi-directional transmitter 1764. The recombined light is thereby directed into a reference module 1768. As shown in the illustrated embodiment, light enters module 1768, passes through lens 1770 and is partially reflected by partial reflector 1772. The light not reflected by partial reflector 1772 passes through lens 1774 before impinging upon mirror 1776, which is set with a configurable distance $Y_{17}$. Light returning from module 1768 passes along fibers 1766 and 1780 to detection module 1782. Generally, detection modules 1760 and 1782 are configured to detect and analyze interference signals based on the combined light returning from the sample and the reference light, to perform OCT motion analysis.

One of ordinary skill in the art will appreciate that the embodiments disclosed in FIGS. 16 and 17 represent advancements in conventional common-path systems. In particular, as described above, systems 1600 and 1700 have been configured to incorporate the principles described herein, especially the addition of multiple scanning beams without also introducing excess complexity.

Figure 18:
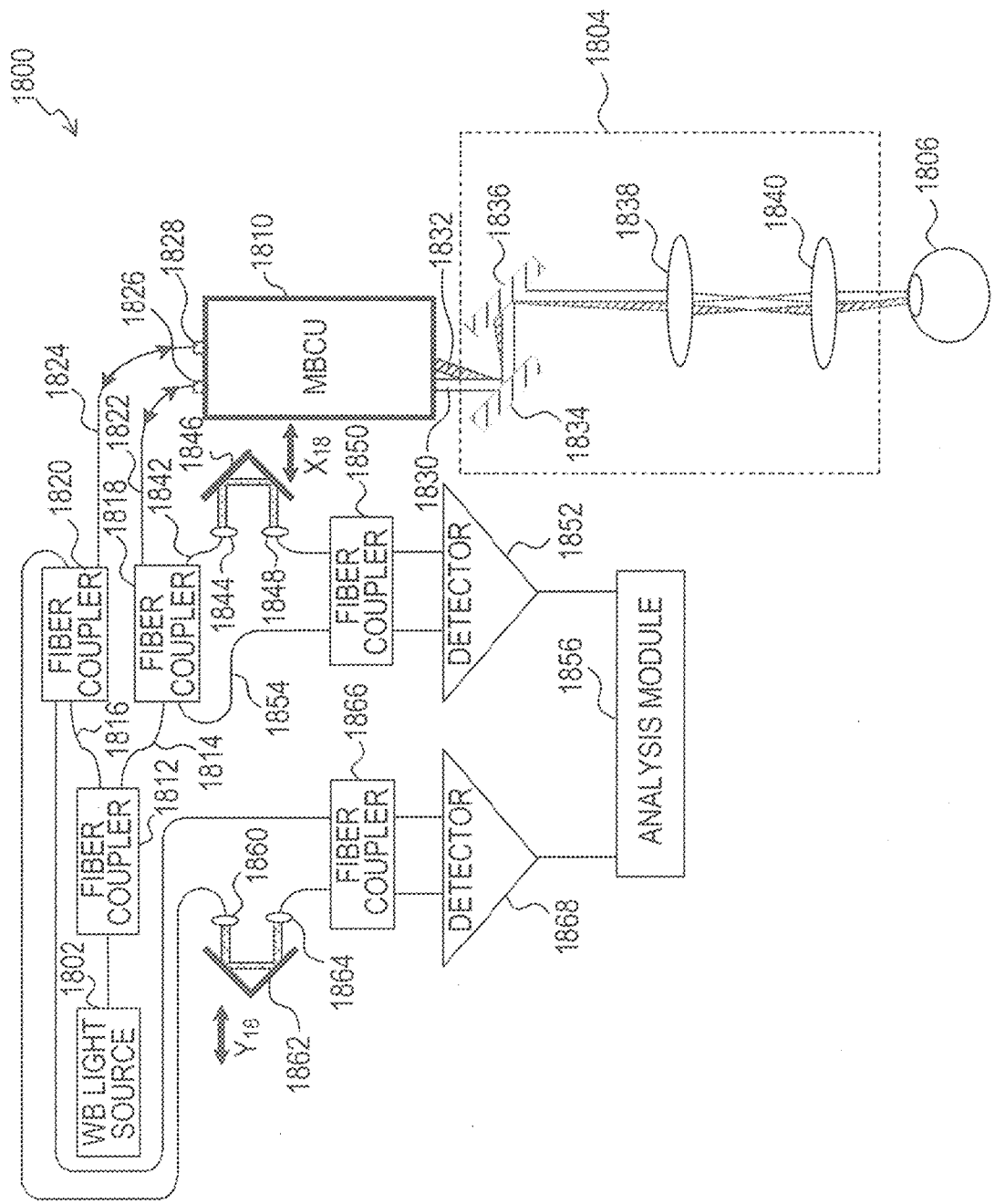
FIG. 18 is a block diagram showing a multi-channel optical coherence tomography apparatus in accordance with still another embodiment.

FIG. 18 is a block diagram showing a multi-channel optical coherence tomography apparatus in accordance with still another embodiment. In particular, FIG. 18 illustrates a system 1800 configured without bi-directional transmitters (circulators). FIG. 18 shows a system 1800 configured with a WB light source 1802, an MBCU 1810, a scan system 1804, configured to scan a sample 1806.

Generally, source 1802 generates source light that is directed to a fiber coupler 1812. Fiber coupler 1812 directs light along fiber 1814 to fiber coupler 1818 and directs light along fiber 1816 to fiber coupler 1820. Generally, fiber coupler 1818 directs light to the MBCU 1810 and a reference path. Similarly, fiber coupler 1820 directs light to the MBCU 1810 and a (different) reference path. For light directed toward the sample, fiber coupler 1818 directs light to port 1826 of MBCU 1810 along fiber 1822. Light entering port 1826 exits MBCU 1810 as beam 1830. Similarly, fiber coupler 1820 directs light to port 1828 of MBCU 1810 along fiber 1824. Light entering port 1828 exits MBCU 1810 as beam 1832.

In the illustrated embodiment, fibers 1822 and 1824 are configured with different optical path lengths. Beams 1830 and 1832 reflect from mirror 1834 to mirror 1836, through lens 1838 and lens 1840, before impinging on sample 1806. In the illustrated embodiment, the light reflecting from the sample returns back through the optical paths to fiber couplers 1818 and 1820.

In the illustrated embodiment, light returning from the sample through fiber coupler 1818 is directed to fiber coupler 1850 through a fiber 1854. As described above, in the illustrated embodiment, fiber coupler 1850 combines light returning from the sample with a reference light from the reference path (lens 1844, mirror 1846, and lens 1848), to generate an interference signal. As illustrated, mirror 1846 can be translated along the direction indicated by arrow $X_{18}$. Detector 1852 receives the interference signal and generates a scan signal for transmission to analysis module 1856. As described above, analysis module 1856 performs optical coherence tomography motion analysis based on the scan signal.

In the illustrated embodiment, light returning from the sample through fiber coupler 1820 is directed to fiber coupler 1866. As described above, in the illustrated embodiment, fiber coupler 1866 combines light returning from the sample with a reference light from the reference path (lens 1860, mirror 1862, and lens 1864), to generate an interference signal. As illustrated, mirror 1862 can be translated along the direction indicated by arrow $Y_{18}$. Detector 1868 receives the interference signal and generates a scan signal for transmission to analysis module 1856. As described above, analysis module 1856 performs optical coherence tomography motion analysis based on the scan signal.

Figure 19:
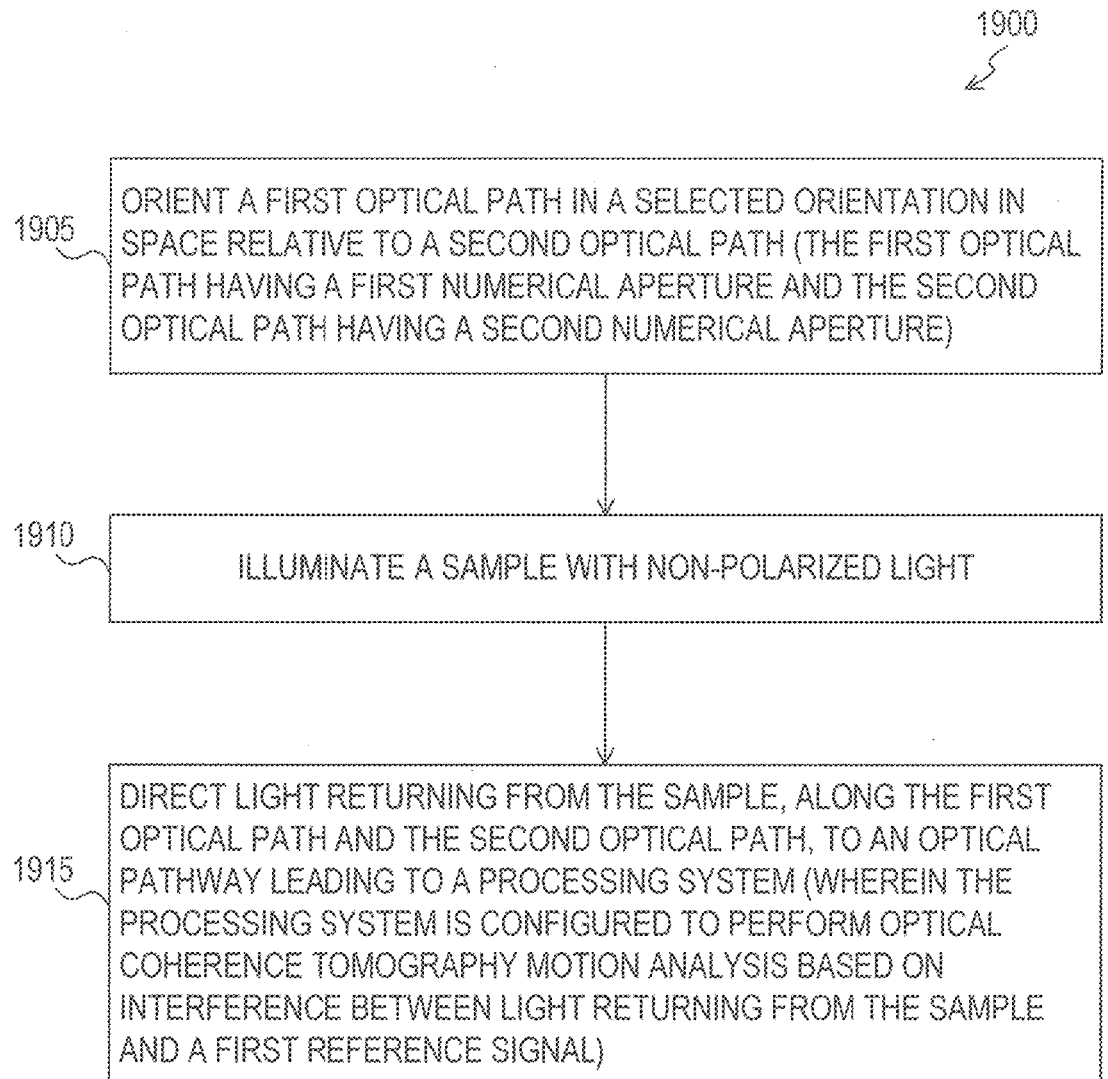
FIG. 19 is a flow diagram showing a multi-channel optical coherence tomography method in accordance with one embodiment.

FIG. 19 illustrates one embodiment of a method for multi-channel optical coherence tomography. Specifically, FIG. 19 illustrates a high-level flow chart 1900 that depicts logical operational steps performed by, for example, system 100 of FIG. 1 or system 200 of FIG. 2, which may be implemented in accordance with a preferred embodiment.

As indicated at block 1905, the process begins and a first optical path is oriented in a selected orientation in space relative to a second optical path. In one embodiment, this step is performed by MBCU 110 of FIG. 1 or MBCU 210 or FIG. 2, for example. In one embodiment, with respect to FIG. 3, the second optical path includes fiber 312 and the first optical path includes the selected fiber 332, this step is performed by plate 314 of FIG. 3 orienting fiber 332 with respect to fiber 312.

As shown at block 1905, the first optical path has a first numerical aperture and the second optical path has a second numerical aperture. In one example embodiment, with respect to FIG. 3, tip lens 336 can be configured with the first numerical aperture and tip lens 318 can be configured with the second numerical aperture.

Next, as shown at block 1910, a sample is illuminated with non-polarized light. In one example embodiment, this step can be performed by scan system 120 of FIG. 1 illuminating sample 104 with beams 112 and 114 from MBCU 110. As described above, beams 112 and 114 are non-polarized light beams.

Next, as shown at block 1915, light returning from the sample is directed, along the first optical path and the second optical path, to an optical pathway leading to a processing system. In one example embodiment, this step can be performed by MBCU 110 receiving returning light from scan system 120 and delivering the returning light at ports 140 and 150 to fibers 138 and 148, where fibers 138 and 148 comprise an optical pathway leading to a processing system. As described above, in one embodiment, the processing system comprises analysis module 180, which is configured to perform optical coherence tomography motion analysis, based on a scan signal from detector 172, which generates the scan signal based on interference between light returning from the sample (from fiber 164) and a first reference signal (from fiber 162), in the form of an interference signal generated by fiber coupler 166.

In another example embodiment, this step can be performed by MBCU 300 receiving returning light from a scan system along the path indicated by beam 322, exit lens 310, beam 320, tip lens 318, and fiber 312 (the second optical path), delivering the returning light to input port 304, which couples to a processing system, such as described above, for example. One having ordinary skill in the art will understand that other configurations, based on the principles described herein, can also be employed.

As described above, the disclosed embodiments have generally been described with respect to two-beam configurations, in order to simplify the disclosure. FIG. 20 is a block diagram showing a multi-beam configuration unit in accordance with yet another embodiment, configured for three-beam OCT. More particularly, FIG. 20 illustrates an MBCU 2000 configured with two optical switches, a plurality of optical fibers and tip lenses, and an exit lens. In the illustrated embodiment, MBCU 2000 includes a frame 2002, configured to provide a structure to which one or more of the various components of MBCU 2000 can be fixed in a static orientation and/or position in space. In an alternate embodiment, frame 2002 can be omitted. In an alternate embodiment, one or more components of MBCU 2000 can be configured outside frame 2002. One of ordinary skill in the art will understand that other configurations can also be employed.

MBCU 2000 includes input ports 2004, 2006, and 2008, which couple to frame 2002. Generally, input ports 2004, 2006, and 2008 are each configured to couple an optical fiber to the components of MBCU 2000, as described in more detail below. In operation, input ports 2004, 2006, and 2008 receive input light, which is passed through to an exit lens 2010 as scanning beams having a desired orientation in space relative to each other.

In the illustrated embodiment, input port 2004 couples received light to an otherwise conventional single mode fiber 2012. A plate 2014 holds fiber 2012 in a fixed orientation relative to exit lens 2010. In the illustrated embodiment, plate 2014 is an otherwise conventional V-groove plate. One of ordinary skill in the art will understand that other suitable mechanisms can be employed to hold fiber 2012 in a fixed orientation.

In the illustrated embodiment, the surface tip of fiber 2012 co-axially couples to a tip lens 2018. In the illustrated embodiment, output beam 2020 of tip lens 2018 impinges upon exit lens 2010 at or near the center of exit lens 2010. In the illustrated embodiment, the resultant beam, output beam 2022, is collimated. Generally, fiber 2012 and tip lens 2018 together comprise an optical path of MBCU 2000.

In the illustrated embodiment, input port 2006 is configured to couple received input light to an otherwise conventional optical switch 2030. In the illustrated embodiment, optical switch 2030 is configured to direct received light to one of three ports 2032, 2034, and 2036. One of ordinary skill in the art will understand that configurations having more or less than three ports can also be employed. Generally, each of optical ports 2032, 2034, and 2036 are configured to route received light along a path having a particular orientation in space relative to the path of optical fiber 2012.

In the illustrated embodiment, ports 2032, 2034, and 2036 are coupled to otherwise conventional single mode fibers 2038, 2040, and 2042, respectively. Fibers 2038 and 2040 are coupled to tip lenses 2046 and 2054, respectively. Fiber 2042 also couples to a tip lens. In the illustrated embodiment, each of fibers 2038, 2040, and 2042 (and their associated tip lenses) are held in a fixed orientation by plate 2014. In the illustrated embodiment, plate 2014 aligns fibers 2038, 2040, and 2042 parallel to each other and to fiber 2012.

So configured, optical switch 2030 can be operated to direct incoming light along one of fibers 2038, 2040, and 2042, thereby selecting one of beams 2048 and 2056, for example. In the illustrated embodiment, beam 2048 has been selected. Each of beams 2048 and 2056 impinge on exit lens 2010, generating beams 2050 and 2058, respectively. One of ordinary skill in the art will understand that smaller inter-fiber distances allow smaller output angles between beams exiting exit lens 2010.

Similarly, in the illustrated embodiment, input port 2008 is configured to couple received input light to an otherwise conventional optical switch 2060. In the illustrated embodiment, optical switch 2060 is configured to direct received light to one of three ports 2062, 2064, and 2066. One of ordinary skill in the art will understand that configurations having more or less than three ports can also be employed. Generally, each of optical ports 2062, 2064, and 2066 are configured to route received light along a path having a particular orientation in space relative to the path of optical fiber 2012.

In the illustrated embodiment, ports 2062, 2064, and 2066 are coupled to otherwise conventional single mode fibers 2068, 2070, and 2072, respectively. Fibers 2068 and 2070 are coupled to tip lenses 2076 and 2084, respectively. Fiber 2072 also couples to a tip lens. In the illustrated embodiment, each of fibers 2068, 2070, and 2072 (and their associated tip lenses) are held in a fixed orientation by plate 2014. In the illustrated embodiment, plate 2014 aligns fibers 2068, 2070, and 2072 parallel to each other and to fiber 2012.

So configured, optical switch 2060 can be operated to direct incoming light along one of fibers 2068, 2070, and 2072, thereby selecting one of beams 2078 and 2086, for example. In the illustrated embodiment, beam 2078 has been selected. Each of beams 2078 and 2086 impinge on exit lens 2010, generating beams 2080 and 2088, respectively. So configured, MBCU 2000 can be operated to independently vary the spatial separation of three beams that impinge on a sample. One having ordinary skill in the art will understand how to extend this principle to accommodate additional scan beams.

Additionally, various beams herein have been described as "collimated." One having ordinary skill in the art will understand that perfectly collimated beams can be cost-prohibitive. As such, one skilled in the art will appreciate that beams sufficiently collimated to make deviations from perfect collimation within the ordinary margin of error can also be employed. Alternatively, beams wherein deviation from perfect collimation does not substantially affect the quality of the measurements can also be employed. Furthermore, in some cases, one having ordinary skill in the art will appreciate that appropriate beams can be substituted with non-collimated beams.

One skilled in the art will appreciate that variations of the above-disclosed and other features and functions, or alternatives thereof, may be desirably combined into many other different systems or applications. Additionally, various presently unforeseen or unanticipated alternatives, modifications, variations or improvements therein may be subsequently made by those having ordinary skill in the art, which are also intended to be encompassed by the following claims.

What is claimed is:

1. An optical coherence tomography apparatus, comprising:
   a multi-beam configuration unit comprising at least a first optical path having a first numerical aperture and a second optical path having a second numerical aperture, the multi-beam configuration unit being configured to orient the second optical path in a selected orientation in space relative to the first optical path;
   a scan system configured to illuminate a sample with non-polarized light received from the multi-beam configuration unit and to direct light returning from the sample to the first optical path and the second optical path; and
   the multi-beam configuration unit being further configured to direct light returning from the sample, along the first optical path and the second optical path, to an optical pathway leading to a processing system;
   wherein the processing system is configured to perform optical coherence tomography motion analysis based on interference between light returning from the sample and a first reference signal.

2. The optical coherence tomography apparatus of claim 1, wherein:

the multi-beam configuration unit is further configured to receive a first sample beam and to direct the first sample beam along the first optical path to the scan system.

3. The optical coherence tomography apparatus of claim 2, wherein:
the multi-beam configuration unit is further configured to receive a second sample beam and to direct the second sample beam along the second optical path to the scan system.

4. The optical coherence tomography apparatus of claim 1, wherein:
the multi-beam configuration unit is further configured to orient the second optical path in a selected orientation in space relative to the first optical path by manipulation of optical components including one of the following:
selecting one of a plurality of optical paths, wherein each optical path comprises a dedicated optical fiber;
moving a first optical fiber in space relative to a second optical fiber; and
moving a mirror to change the angle at which light from the first optical path intersects light from the second optical path.

5. The optical coherence tomography apparatus of claim 1, wherein:
the multi-beam configuration unit is further configured to control the orientation of the first active beam to impinge upon a point on the scan system at a first angular displacement and to control the orientation of the second active beam to impinge upon the point on the scan system at a second angular displacement; and
wherein the first active beam and the second active beam impinge upon the sample at locations separated by a interval based on the difference between the first angular displacement and the second angular displacement.

6. The optical coherence tomography apparatus of claim 1, wherein:
the multi-beam configuration unit is further configured to control the orientation of the first active beam to impinge upon a first scan point on the scan system at a first location and to control the orientation of the second active beam to impinge upon a second scan point on the scan system at a second location;
wherein the first location and the second location are separated by an interval;
wherein the first active beam and the second active beam impinge upon the scan system in a parallel orientation in a first plane;
wherein the first active beam impinges upon the sample at a sample point with a first angular displacement, the first angular displacement based on the first location; and
wherein the second active beam impinges upon the sample at the sample point with a second angular displacement, the second angular displacement based on the second location.

7. The optical tomography apparatus of claim 6, wherein:
the multi-beam configuration unit is further configured to control the orientation of the first active beam to impinge upon a third scan point on the scan system at a third location and to control the orientation of the second active beam to impinge upon a fourth scan point on the scan system at a fourth location;
wherein the third location and the fourth location are separated by an interval; and
wherein the first active beam, when oriented to illuminate the third scan point, and the second active beam, when oriented to illuminate the fourth scan point, impinge upon the scan system in a parallel orientation in a second plane, wherein the second plane perpendicular to the first plane.

8. The optical coherence tomography apparatus of claim 1, further comprising:
a reference arm coupled to the multi-beam configuration unit and the processing system, the reference arm being configured to generate the first reference signal.

9. The optical coherence tomography apparatus of claim 1, further comprising a partial reflector configured to reflect a portion of the first active beam and the second active beam, to generate a first reference signal, the first reference signal being one of the at least one reference signal.

10. The optical coherence tomography apparatus of claim 1, wherein:
the processing system comprises a first detector configured to generate a first scan signal based on interference between a first part of light returning from the sample and the first reference signal; and
wherein the processing system further comprises a second detector configured to generate a second scan signal based on interference between a second part of light returning from the sample and a second reference signal.

11. The optical coherence tomography apparatus of claim 1, wherein:
the multi-beam configuration unit further comprises a third optical path, the multi-beam configuration unit being further configured to arrange the third optical path in a selected second orientation; and
wherein the scanning module is further configured to scan the sample with the third active beam simultaneously with the first active beam and the second active beam.

12. An optical coherence tomography method, comprising:
orienting a first optical path in a selected orientation in space relative to a second optical path;
the first optical path having a first numerical aperture and the second optical path having a second numerical aperture;
illuminating a sample with non-polarized light; and
directing light returning from the sample, along the first optical path and the second optical path, to an optical pathway leading to a processing system;
wherein the processing system is configured to perform optical coherence tomography motion analysis based on interference between light returning from the sample and a first reference signal.

* * * * *